United States Patent
Heine et al.

(10) Patent No.: US 8,809,345 B2
(45) Date of Patent: Aug. 19, 2014

(54) 6-CYCLOALKYL-PYRAZOLOPYRIMIDI-NONES FOR THE TREATMENT OF CNS DISORDERS

(75) Inventors: Niklas Heine, Biberach (DE); Riccardo Giovannini, Verona (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 183 days.

(21) Appl. No.: 13/369,596

(22) Filed: Feb. 9, 2012

(65) Prior Publication Data
US 2013/0040955 A1  Feb. 14, 2013

(30) Foreign Application Priority Data

Feb. 15, 2011 (EP) .................................. 11154572
Feb. 17, 2011 (EP) .................................. 11154858

(51) Int. Cl.
*C07D 519/00* (2006.01)
*A61K 31/519* (2006.01)
*C07D 487/04* (2006.01)
*A61P 25/28* (2006.01)
*A61P 25/16* (2006.01)
*A61P 25/18* (2006.01)

(52) U.S. Cl.
CPC ............ *C07D 487/04* (2013.01); *C07D 519/00* (2013.01)
USPC ....................... 514/259.3; 514/262.1; 544/262

(58) Field of Classification Search
CPC ....................................................... C07D 519/00
USPC ........................................ 544/262; 514/262.1
See application file for complete search history.

(56) References Cited

U.S. PATENT DOCUMENTS

| | | |
|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,244,328 A | 4/1966 | Brown |
| 3,732,225 A | 5/1973 | Breuer et al. |
| 3,847,908 A | 11/1974 | Breuer et al. |
| 3,884,906 A | 5/1975 | Van Der Meer et al. |
| 4,602,023 A | 7/1986 | Kiely et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,113,855 A | 5/1992 | Newhouse |
| 5,201,308 A | 4/1993 | Newhouse |
| 5,239,992 A | 8/1993 | Bougamont et al. |
| 5,256,668 A | 10/1993 | Hsu et al. |
| 5,270,315 A | 12/1993 | Belleau et al. |
| 5,294,612 A | 3/1994 | Bacon et al. |
| 5,341,801 A | 8/1994 | Zechner |
| 5,466,806 A | 11/1995 | Belleau et al. |
| 5,503,144 A | 4/1996 | Bacon |
| 5,541,187 A | 7/1996 | Bacon et al. |
| 5,563,049 A | 10/1996 | Kojima et al. |
| 5,568,884 A | 10/1996 | Bruna |
| 5,634,900 A | 6/1997 | Makino et al. |
| 5,656,629 A | 8/1997 | Bacon et al. |
| 5,684,164 A | 11/1997 | Belleau et al. |
| 5,750,673 A | 5/1998 | Martin |
| 5,948,812 A | 9/1999 | Kraft |
| 5,969,116 A | 10/1999 | Martin |
| 5,969,499 A | 10/1999 | Shaffer |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |

(Continued)

FOREIGN PATENT DOCUMENTS

| | | |
|---|---|---|
| CA | 2090227 A1 | 3/1992 |
| CA | 1311201 C | 12/1992 |
| CA | 2283211 A1 | 9/1998 |
| CA | 2238211 A1 | 12/1998 |
| CA | 2357146 A1 | 7/2000 |

(Continued)

OTHER PUBLICATIONS

Accessed on Dec. 18, 2008: wikipedia: "Amnesia", http://www.mentalhealth.org.uk/information/mental-health-a-z/dementia/, last accessed on Dec. 18, 2008.

(Continued)

*Primary Examiner* — Susanna Moore
(74) *Attorney, Agent, or Firm* — Michael P. Morris; Edward S. Lazer

(57) ABSTRACT

The invention relates to novel pyrazolopyrimidinones according to formula (I):

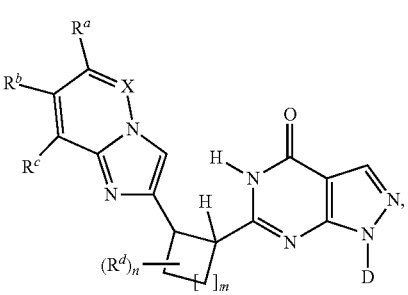

wherein X, D, $R^a$, $R^b$, $R^c$, $R^d$, $R^e$, m and n are as defined herein. The invention also relates to pharmaceutical compositions comprising these compounds and methods of using these compounds in the treatment of various diseases concerning deficits in perception, concentration, learning or memory.

13 Claims, No Drawings

(56) References Cited

U.S. PATENT DOCUMENTS

| | | |
|---|---|---|
| 6,479,463 B1 | 11/2002 | Wang et al. |
| 6,831,174 B2 | 12/2004 | Belleau et al. |
| 6,903,224 B2 | 6/2005 | Belleau et al. |
| 7,022,709 B2 | 4/2006 | Boss et al. |
| 7,067,507 B2 | 6/2006 | Pulley et al. |
| 7,122,693 B2 | 10/2006 | Belleau et al. |
| 7,375,213 B2 | 5/2008 | Deshpande et al. |
| 7,488,733 B2 | 2/2009 | Hendrix et al. |
| 7,488,766 B2 | 2/2009 | Peters et al. |
| 7,541,341 B2 | 6/2009 | Fushimi et al. |
| 7,579,449 B2 | 8/2009 | Eckhardt et al. |
| 7,615,558 B2 | 11/2009 | Hendrix et al. |
| 7,662,790 B2 | 2/2010 | Himmelsbach et al. |
| 7,683,160 B2 | 3/2010 | Eckhardt et al. |
| 7,687,469 B2 | 3/2010 | Eckhardt et al. |
| 7,708,011 B2 | 5/2010 | Hochrainer et al. |
| 7,713,938 B2 | 5/2010 | Himmelsbach et al. |
| 7,723,309 B2 | 5/2010 | Himmelsbach et al. |
| 7,737,156 B2 | 6/2010 | Boβ et al. |
| 7,745,414 B2 | 6/2010 | Eckhardt et al. |
| 7,772,191 B2 | 8/2010 | Eckhardt et al. |
| 7,772,378 B2 | 8/2010 | Himmelsbach et al. |
| 7,776,830 B2 | 8/2010 | Eckhardt et al. |
| 7,847,074 B2 | 12/2010 | Eckhardt et al. |
| 7,851,602 B2 | 12/2010 | Himmelsbach et al. |
| 7,858,587 B2 | 12/2010 | Eckhardt et al. |
| 7,870,856 B2 | 1/2011 | Boeck |
| 7,879,806 B2 | 2/2011 | Himmelsbach et al. |
| 7,879,807 B2 | 2/2011 | Himmelsbach et al. |
| 7,984,713 B2 | 7/2011 | Hochrainer et al. |
| 8,039,441 B2 | 10/2011 | Himmelsbach et al. |
| 8,039,477 B2 | 10/2011 | Hendrix et al. |
| 8,044,060 B2 | 10/2011 | Hendrix et al. |
| 8,088,769 B2 | 1/2012 | Hendrix et al. |
| 2001/0041797 A1 | 11/2001 | Belleau et al. |
| 2001/0044441 A1 | 11/2001 | Campbell et al. |
| 2002/0016348 A1 | 2/2002 | Simitchieva et al. |
| 2002/0074774 A1 | 6/2002 | Hsu et al. |
| 2002/0086160 A1 | 7/2002 | Qiu et al. |
| 2002/0100222 A1 | 8/2002 | Koenig et al. |
| 2002/0132754 A1 | 9/2002 | Boss et al. |
| 2002/0137903 A1 | 9/2002 | Ellsworth et al. |
| 2003/0064935 A1 | 4/2003 | Gougoutas |
| 2003/0087918 A1 | 5/2003 | Belleau et al. |
| 2003/0114390 A1 | 6/2003 | Washburn et al. |
| 2003/0195205 A1 | 10/2003 | DeNinno et al. |
| 2004/0185459 A1 | 9/2004 | Otsuka et al. |
| 2004/0187868 A1 | 9/2004 | Hochrainer et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0187168 A1 | 8/2005 | Eickelmann et al. |
| 2005/0209251 A1 | 9/2005 | Linker et al. |
| 2005/0233982 A1 | 10/2005 | Himmelsbach et al. |
| 2005/0263151 A1 | 12/2005 | Hochrainer et al. |
| 2006/0009400 A1 | 1/2006 | Eckhardt et al. |
| 2006/0025349 A1 | 2/2006 | Eckhardt et al. |
| 2006/0074031 A1 | 4/2006 | Eckhardt et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2007/0240713 A1 | 10/2007 | Boeck |
| 2007/0281940 A1 | 12/2007 | Dugi et al. |
| 2008/0255118 A1 | 10/2008 | Hendrix et al. |
| 2009/0023913 A1 | 1/2009 | Eckhardt et al. |
| 2009/0111838 A1 | 4/2009 | Hendrix et al. |
| 2009/0121919 A1 | 5/2009 | Kihara |
| 2009/0194105 A1 | 8/2009 | Besseler et al. |
| 2009/0235929 A1 | 9/2009 | Egen et al. |
| 2009/0318547 A1 | 12/2009 | Eckhardt et al. |
| 2009/0326215 A1 | 12/2009 | Eckhardt et al. |
| 2010/0024815 A1 | 2/2010 | Kladders |
| 2010/0035900 A1 | 2/2010 | Hendrix et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0210839 A1 | 8/2010 | Boss et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015193 A1 | 1/2011 | Eickmeier et al. |
| 2011/0046076 A1 | 2/2011 | Eickelmann et al. |
| 2011/0046087 A1 | 2/2011 | Eickelmann et al. |
| 2011/0065730 A1 | 3/2011 | Hendrix et al. |
| 2011/0065731 A1 | 3/2011 | Dugi et al. |
| 2011/0082137 A1 | 4/2011 | Giovannini et al. |
| 2011/0098240 A1 | 4/2011 | Dugi et al. |
| 2011/0178033 A1 | 7/2011 | Eckhardt et al. |
| 2011/0184000 A1 | 7/2011 | Giovannini et al. |
| 2011/0203586 A1 | 8/2011 | Egen et al. |
| 2011/0207735 A1 | 8/2011 | Hendrix et al. |
| 2011/0212960 A1 | 9/2011 | Heine et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2011/0294834 A1 | 12/2011 | Hendrix et al. |
| 2012/0010224 A1 | 1/2012 | Hendrix et al. |
| 2012/0115863 A1 | 5/2012 | Fuchs et al. |
| 2012/0165349 A1 | 6/2012 | Hendrix et al. |
| 2012/0202829 A1 | 8/2012 | Heine et al. |

FOREIGN PATENT DOCUMENTS

| | | |
|---|---|---|
| CA | 2437240 A1 | 8/2002 |
| CA | 2438890 A1 | 9/2002 |
| CA | 2417631 A1 | 1/2003 |
| CA | 2466824 A1 | 5/2003 |
| CA | 2484997 A1 | 11/2003 |
| CA | 2496194 A1 | 3/2004 |
| CA | 2496292 A1 | 4/2004 |
| CA | 2496306 A1 | 4/2004 |
| CA | 2496308 A1 | 4/2004 |
| CA | 2524900 A1 | 11/2004 |
| CA | 2539032 A1 | 3/2005 |
| CH | 396923 A | 8/1965 |
| CH | 396924 A | 8/1965 |
| CH | 396925 A | 8/1965 |
| CH | 396926 A | 8/1965 |
| CH | 396927 A | 8/1965 |
| CH | 398626 A | 3/1966 |
| DE | 1147234 B | 4/1963 |
| DE | 1149013 B | 5/1963 |
| DE | 1153023 B | 8/1963 |
| DE | 1156415 B | 10/1963 |
| DE | 2408906 A1 | 9/1974 |
| DE | 4004558 A1 | 9/1990 |
| DE | 4027391 A1 | 3/1992 |
| DE | 10156249 A1 | 5/2003 |
| DE | 10238722 A1 | 3/2004 |
| EP | 0130735 A1 | 1/1985 |
| EP | 0286028 A2 | 10/1988 |
| EP | 0496617 A1 | 7/1992 |
| EP | 0516510 A1 | 12/1992 |
| EP | 0546996 A2 | 6/1993 |
| EP | 0626387 A1 | 11/1994 |
| EP | 0679657 A2 | 11/1995 |
| EP | 0995751 A2 | 4/2000 |
| EP | 1460077 A1 | 9/2004 |

(56) References Cited

FOREIGN PATENT DOCUMENTS

| | | |
|---|---|---|
| GB | 937723 A | 9/1963 |
| GB | 937724 A | 9/1963 |
| GB | 937726 A | 9/1963 |
| GB | 973361 A | 10/1964 |
| JP | 2001513638 A | 9/2001 |
| JP | 2001514638 A | 9/2001 |
| JP | 2002523507 A | 7/2002 |
| JP | 2004536933 A | 12/2004 |
| JP | 2005531549 A | 10/2005 |
| JP | 2006501272 A | 1/2006 |
| JP | 2006503051 A | 1/2006 |
| WO | 9414802 A1 | 7/1994 |
| WO | 9417803 A1 | 8/1994 |
| WO | 9510506 A1 | 4/1995 |
| WO | 9628429 A1 | 9/1996 |
| WO | 9716456 A1 | 5/1997 |
| WO | 9746569 A2 | 12/1997 |
| WO | 9800434 A1 | 1/1998 |
| WO | 9810765 A1 | 3/1998 |
| WO | 9816184 A2 | 4/1998 |
| WO | 9840384 A1 | 9/1998 |
| WO | 9941253 A1 | 8/1999 |
| WO | 0018758 A1 | 4/2000 |
| WO | 0043394 A1 | 7/2000 |
| WO | 0160315 A2 | 8/2001 |
| WO | 0177075 A2 | 10/2001 |
| WO | 0206288 A1 | 1/2002 |
| WO | 0209713 A2 | 2/2002 |
| WO | 0216348 A1 | 2/2002 |
| WO | 02055082 A1 | 7/2002 |
| WO | 02057425 A2 | 7/2002 |
| WO | 02068423 A1 | 9/2002 |
| WO | 02074774 A1 | 9/2002 |
| WO | 02086160 A1 | 10/2002 |
| WO | 02098864 A1 | 12/2002 |
| WO | 03011923 A1 | 2/2003 |
| WO | 03011925 A1 | 2/2003 |
| WO | 03022859 A2 | 3/2003 |
| WO | 03031458 A1 | 4/2003 |
| WO | 03037432 A1 | 5/2003 |
| WO | 03037899 A1 | 5/2003 |
| WO | 03041725 A2 | 5/2003 |
| WO | 03072757 A2 | 9/2003 |
| WO | 03093269 A2 | 11/2003 |
| WO | 03099840 A1 | 12/2003 |
| WO | 2004002999 A2 | 1/2004 |
| WO | 2004018474 A1 | 3/2004 |
| WO | 2004026286 A2 | 4/2004 |
| WO | 2004026876 A1 | 4/2004 |
| WO | 2004046331 A2 | 6/2004 |
| WO | 2004096811 A1 | 11/2004 |
| WO | 2004099210 A1 | 11/2004 |
| WO | 2004099211 A1 | 11/2004 |
| WO | 2004108139 A2 | 12/2004 |
| WO | 2004113306 A1 | 12/2004 |
| WO | 2005021566 A2 | 3/2005 |
| WO | 2005051944 A1 | 6/2005 |
| WO | 2005068436 A1 | 7/2005 |
| WO | 2006076455 A2 | 7/2006 |
| WO | 2006084281 A1 | 8/2006 |
| WO | 2006091905 A1 | 8/2006 |
| WO | 2006125548 A1 | 11/2006 |
| WO | 2007025043 A2 | 3/2007 |
| WO | 2007046747 A1 | 4/2007 |
| WO | 2008005542 A2 | 1/2008 |
| WO | 2008049923 A1 | 5/2008 |
| WO | 2008055959 A1 | 5/2008 |
| WO | 2008100447 A2 | 8/2008 |
| WO | 2008104077 A1 | 9/2008 |
| WO | 2008139293 A1 | 11/2008 |
| WO | 2009068617 A1 | 6/2009 |
| WO | 2009121919 A1 | 10/2009 |
| WO | 2010026214 A1 | 3/2010 |
| WO | 2010092123 A1 | 8/2010 |
| WO | 2010092125 A1 | 8/2010 |
| WO | 2010112437 A1 | 10/2010 |
| WO | 2011018495 A1 | 2/2011 |

OTHER PUBLICATIONS

Accessed on Jun. 30, 2008, Intelihealth: "Alzheimer's Disease," http://www.intelihealth.com/IH/ihtIH/WSIHW/8303/9117/195703.html?d=dmtHelathAZ.

Accessed on Sep. 22, 2009: Intelihealth: "Dementia," http://www.intelihealth.com/IH/ihtIH/WSIHW000/244798/00084.html.

Accessed on Sep. 22, 2009: Intelihealth: "Parkinson's Disease", http://www.intelihealth.com/IH/htIH?d=dmtHealthAZ&c=201957.

Andreeva, Svetlana G, et al; "Expression of cGMP-Specific Phosphodiesterase 9A ...", J. of Neuroscience, 2001, Vo. 21, No. 22, pp. 9068-9076.

Bagli, Jehan et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Barger, Steven, W; Role of Cyclic GMP in the Regulation of Neuronal Calcium and Survival by Secreted Forms of Beta-Amyloid Precursor; Journal of Neurochemistry (1995) vol. 64, No. 5, pp. 2087-2096.

Bernabeu, R., et al; Hippocampal cGMP and cAMP are Differentially Involved in Memory Processing of Inhibitors Avoidance Learning; Neuroreport (1996) vol. 7, No. 2 pp. 585-588.

Byrn, Stephen, R; Solid State Chemistry of Drugs (1999) vol. 2, No. 10, pp. 232-247.

Caligiuri, Maureen, et al; A ProTeome-Wide CDK/CRK-Specific Kinase inhibitor Promotes Tumor Cell Death in the Absence of Cell Cycle Progression; Chemistry & Biology (2005) vol. 12 pp. 1103-1115.

Chem Abstracts Service, Database Accession No. ALB-H01677136, Database Chemcats, 2007, XP002556399.

Cheng, C. C. et al; Potential Purine Antagonists VII. Synthesis of 6-Alkylpyrazolo-[3,4-d]pyrimidinesn Potential Purine Antagonist VII; Gazz. Chim. Ital., (1958) vol. 23, pp. 191-200.

Ciba Geigy AG, "Nucleosides and oligonucleotides and 2'-ether groups," Data Supplied from the espacenet database, Publication Date: Nov. 30, 1994; English Abstract of EPO 626 387.

DeNinno et al. "The discovery of potent, selective, and orally bioavailable PDE9 ...", Bioorganic & Medicinal Chemistry Letters, 2009, vol. 19, pp. 2537-2541.

Doerwald et al., "Side reactions in organic synthesis," A Guide to Successful Synthesis Design, 2005, 4 pages.

Ebert et al., "Scopolamine model of demential: electroencephalogram findings and cognitive performance," Europ J of Clinical Investigation, 1998, vol. 28, No. 11, pp. 944-949.

Farlow, Martin, R; Pharmacokinetic Profiles of Currect Therapies for Alzheimer's Disease: Implications for Switching to Galantamine; Clinical Therapeutics (2001) vol. 23, Suppl. A, pp. A13-A-24.

Fawcett, Lindsay et al; "Molecular Cloning and Characterization of a Distinct Human ...", Proc. Natl. Acad. Science, 2000, vol. 97, No. 7, pp. 3702-3707.

Fischer, Douglas A., et al; "Isolation and Characterization of PDE9A, A Novel ...", J. of Biological Chemistry, 1998, vol. 273, No. 25, pp. 15559-15564.

Fisher, Douglas A, et al; "Isolation and Characterization of PDE8A, a Novel ...", Biochemical and Biophysical Research Communications, 1998, vol. 246, pp. 570-577.

Francis et al; Cortical Pyramidal Neurone Loss May Cause Glutamatergic Hypoativity and Cognitive Impairment in Alzheimer's Disease: investigative and Therapeutic Perspectives; Journal of Neurochemistry (1993) vol. 60, No. 5, pp. 1589-1604.

Francis, Paul T; "Glutamatergic Systems in Alzheimer's Disease" International Journal of Geriatic Psychiatry (2003) vol. 18, pp. S15-S21.

Francis, Sharron H., et al; "Characterization of a Novel cGMP Binding Protein form Rat Lung ...", J. of Biological Chemistry, vol. 255, No. 2, pp. 620-626, (1979).

(56) References Cited

OTHER PUBLICATIONS

Fujhishige et al; Cloning and Characterization of a Novel Human Phosphodiesterase That Hydrolyzes Both cAMP and cGMP (PDE10A); Journal of Bilogical Chemistry (1999) vol. 274, No. 26, pp. 18438-18445.
Gielen, Hieke et al; A Novel Approach to Amidines from Esters; Tetrahedron Letters (2002) vol. 43 pp. 419-421.
Gillespie et al; Characterization of a Bovine Cone Photoreceptor Phosphodiesterase Purified by Cyclic Cyclic GMP-Sepharose Chromatography; J. of Biological Chemistry (1988) vol. 263, No. 17, pp. 8133-8141.
Gompper, Rudolf et al; Substituted Dithiocarboxylic Acids and Ketene Thioacetals; Institute for Organic Chemistry Technology (1962) vol. 95, pp. 2861-2870. German & English Translation.
Guipponi, Michel et al; Identification and Characterization of a Novel Cyclic Nucleotide Phosphodiesterase Gene (PDE9A) that Maps to 21q22.3: Alternative Splicing of mRNA Transcripts, Genomic Structure and Sequence; Hum Genet (1998) vol. 103, pp. 386-392.
Harb, A.-F. A., et al; Pyrazoles as Building Blocks in Heterocyclic Synthesis: Synthesis of Some Ne Substituted 1-Triazinylpyrazolo[3,4-d]pyrimidine and 1-Triazinylpyrazolo[3,4-b]pyridine Derivates; Chemical Papers (2005) vol. 59, No. 3, pp. 187-195.
Hendrix et al; "6-cyclymethyl-and 6-alkylmethyl-Substituted Pyrazolopyrimidines," Publication Date: Nov. 18, 2004, Data Supplied from the espacenet database Worlwide; Englsh Abstract of WO 2004099211.
Hendrix et al; "Use of Pyrazolopyrimidine Against Cardiovascular Disease," Publication Date: Nov. 30, 2006, Data Supplied from the espacenet database Worldwide; English Abstract or WO 20060125548.
Hetman, J. M., et al; Cloning and Characterization of PDE7B, a cAMP-Specific Phosphodiesterase; Proc, Natl. Acad. Science (2000) vol. 97, No. 1, pp. 472-476.
http://www.nlm.nih.gov/medlineplus/ency/article/000746.htm, last accessed Jul. 15, 2010.
Huettner et al; Primary Culture of Identified Neurons from the Visual Cortex of Postnatal Rats; Journal of Neuroscience (1986) vol. 6, No. 10, pp. 3044-3060.
Hung et al., "A high-yielding synthesis of monalkylhydrazines," Journal of Organic Chemistry, 1981, vol. 46, pp. 5413-5414.
International Search Report for PCT/EP2008/066350 dated Feb. 23, 2009.
International Search Report for PCT/EP2009/053907 dated May 26, 2009.
International Search Report for PCT/EP2009/061455 dated Mar. 17, 2011.
International Search Report for PCT/EP2010/054050 dated May 27, 2010.
International Search Report for PCT/EP2010/061735 dated Sep. 24, 2010.
International Search Report for PCT/EP2004/006477 dated Oct. 27, 2004.
International Search Report for PCT/EP2004/014872 dated May 19, 2005.
International Search Report of PCT/EP2003/08880 dated Apr. 16, 2004.
International Search Report of PCT/EP2003/08923 dated Dec. 15, 2003.
International Search Report of PCT/EP2003/08979 dated Nov. 25, 2003.
International Search Report of PCT/EP2004/004412 dated Jul. 14, 2004.
International Search Report of PCT/EP2004/004455 dated Sep. 17, 2004.
Loughney, Kate, et al; Isolation and Characterization of cDNAs Corresponding to Two human Calcium, Calmodulin-regulated, 3' ,5'-Cyclic Nucleotide Phosphodiesterases; The Journal of Biological Chemistry (1996) vol. 271, No. 2, pp. 796-806.
Loughney, Kate, et al; Isolation and Characterization of cDNAs Encoding PDE5A, a Human cGMP-Bing, cGMP-Specific 3',5'-cyclic Nucleotide Phosphodiesterase; Gene (1998) vol. 216, pp. 139-147.
Lugnier, Claire; Cyclic Nucleotide Phosphodiesterase (PDE) Superfamily: A New Target for the Development of Specific Therapeutic Agents; Pharmacology & Therapeutics; (2006) vol. 109, pp. 366-398.
Markwalder, J. A. et al; Synthesis and Biological Evaluation of 1-Aryl-4,5-dihydro-1H-pyrazolo[3,4-d]pyrimidin-4-one Inhibitors of Cyclin-Dependent Kinases; J. of Med Chemistry (2004) vol. 47, pp. 5894-5911.
Martins, Timothy, J., et al; Purification and Characterization of a Cyclic GMP-stimulated Cyclic Nucleotide Phosphodiesterase from Bovine Tissues; The Journal of Biological Chemistry (1982) vol. 257, No. 4, pp. 1973-1979.
Merriam-Webster's Collegiate Dictionary, published 1998 by Merriam-Webster Inc. p. 924.
Miki, Takashi, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.
Miyashita, A., et al; Studies on Pyrazolo[3,4-d]pyrimidine Derivatives XVIII Facile Preparation of 1H-Pyrazolo[3,4-d] Pyrimidin-4(5H)-Ones; Heterocycles (1990) vol. 31, No. 7, pp. 1309-1314.
Murashima, Seiko., et al; Characterization of Particulate Cyclic Nucleotide Phosphodiesterases from Bovine Brain: Purification of a Distinct cGMP-Stimulated Isoenzyme; Biochemistry (1990) vol. 29, No. 22, pp. 5285-5292.
Obernolte, Rena, et al; The cDNA of a Human Lymphocyte Cyclic AMP Phosphodiesterase (PDE IV) Reveals a Multigene Family; Gene (1993) vol. 129, pp. 239-247.
Podraza, Kenneth F.; Reductive Cyclization of Ketoesters Utilizing Sodium Cyanoborohydride: Synthesis of ?- and ?-Lactones; J. Heterocyclic Chem (1987) vol. 24. pp. 293.
Prickaerts et al; Possible Role of Nitric Oxide-Cyclic GMP Pathway in Object Recognition Memory: Effects of 7 Nitroindazole and Zaprinast; Europ J of Pharmacology (1997) vol. 337, No. 2-3, pp. 125-136.
Prickaerts, J. et al; Effects of Two Selective Phosphodiesterase Type 5 Inhibitors, Sildenafil and Vardenafil, on Object Recognition Memory and Hippocampal Cyclic GMP Levels in the Rat, Neuroscience (2002) vol. 113, No. 2, pp. 351-361.
Puzzo, Daniela, et al; Amyloid-b Peptide Inhibits Activation of the Nitric Oxide/cGMP/cAMP-Responsive Element-Binding Protein Pathway During Hippocampal Synaptic Plasticity; The Journal of Neuroscience (2005) vol. 25, No. 29, pp. 6887-6897.
Reddy, K. Hemender et al; Versatile Synthesis of 6-Alkyl/Aryl-1H-Pyrazolo[3,4-d]Pyrimidin-4[5H]-Ones; Indian Journal of Chemistry (1992) vol. 31B, pp. 163-166.
Reid I. A.; Role of Phosphodiesterase Isozymes in the Control of Renin Secretion: Effects of Selective Enzyme Inhibitors; Current Pharmaceutical Design (1999) vol. 5, No. 9, pp. 725-735.
Related U.S. Appl. No. 12/855,129, filed Aug. 12, 2010.
Related U.S. Appl. No. 12/935,686, filed Sep. 30, 2010.
Related U.S. Appl. No. 13/062,625, filed Mar. 7, 2011.
Related U.S. Appl. No. 13/099,064, filed May 2, 2011.
Rentero, Carles, et al; Identification and Distribution of Different mRNA Variants Produced by Differential Splicing in the Human Phosphodiesterase 9A Gene; Biochemical and Biophysical Research Communications (2003) vol. 301 pp. 686-692.
Reymann, Klaus, et al; The Late Maintenance of Hippocampal LTP: Requirements, Phases, 'Synaptic Tagging', 'Late-Associativity' and Implications; Neuropharmacology (2007) vol. 52, pp. 24-40.
Roenn, Magnus et al; Palladium (II)-Catalyzed Cyclization Using Molecular Oxygen as Reoxidant; Tetrahedron Letters (1995) vol. 36, No. 42, pp. 7749-7752.
Rosman, Guy, J., et al; Isolation and Characterization of Human cDNSs Encoding a cGMP-Stimulated 3' ,5'-Cyclic Nucleotide Phosphodiesterase; Gene (1997) vol. 191, pp. 89-95.
Schmidt, Richard, R. et al; Pyrazolo[3, 4-d]Pyrimidin-Nucleoside; Chemische Berichte (1977) vol. 110, pp. 2445-2455.

(56) References Cited

OTHER PUBLICATIONS

Schmidt, von P., et al; Heilmittelchemische Studien in der Heterocyclischen Reihe; Helvetica Chimica Acta (1962) vol. 62, No. 189, pp. 1620-1627.
Schousboe, Arne et al; Role of Ca++ and Other Second Messengers in Excitatory Amino Acid Receptor Mediated Neuogeneration: Clinical Perspective; Clinical Neuroscience (1997) vol. 4, pp. 194-198.
Skipper, Howard, E., et al; Structure-Activity Relationships Observed on Screening a Series of Pyrazolopyrimidines Against Experimental Neoplasms; Cancer Research (1957) vol. 17, pp. 579-596.
Soderling, Scott, H. et al; Identification and Characterization of a Novel Family of Cyclic Nucleotide Phosphodiesterases; The Journal of Biological Chemistry (1998) vol. 273, No. 25, pp. 15553-15558.
Soderling, Scott, H. et al; Regulation of cAMP and cGMP signalling: New Phosphodiesterases and New Functions; Current Opinion in Cell Biology (2000) vol. 12, pp. 174-179.
Thomson Innovation Record View, Publication Date: Apr. 18, 1963; English Abstract of DE 1147234B.
Thomson Innovation Record View, Publication Date: Aug. 15, 1965; English Abstract of CH 396 923.
Thomson Innovation Record View, Publication Date: May 22, 1963; English Abstract of DE 1149013B.
Timberlake, J.W. et al; Preparative Procedures: Chemistry of Hydrazo-, Azo-, and Azoxy Groups; Patai (1975) Chapter 4, pp. 69-107.
U.S. Appl. No. 12/545,175, filed Aug. 21, 2009, Inventor: Matthias Eckhardt.
U.S. Appl. No. 12/892,310, filed Sep. 28, 2010. Inventor: Dirk Weber.
U.S. Appl. No. 12/892,326, filed Sep. 28, 2010. Inventor: Dirk Weber.
U.S. Appl. No. 12/894,385, filed Sep. 30, 2010. Inventor: Peter Schneider.
U.S. Appl. No. 13/079,424, filed Apr. 4, 2011. Inventor: Matthias Eckhardt.
U.S. Appl. No. 13/369,596, filed Feb. 9, 2012. Inventor: Niklas Heine.
U.S. Appl. No. 13/369,623, filed Feb. 9, 2012. Inventor: Niklas Heine.
Ugarkar, Bheemarao, et al; Synthesis and antiviral/Antitumor Activities of Certain Pyrazolo[3,4-d]pyrimidine-4 (5H)-selone Nucleosides and Related compounds; Journal of Medicinal Chemistry (1984) vol. 27, No. 8, pp. 1026-1030.
Ulrich, Joachim; Crystallization; Kirk-Othmer Encyclopedia of Chem Techn (2002) 7 pages.
Van Der Staay, F. Josef., et al; The Novel Selective PDE9 Inhibitor BAY 73-6691 Improves Learning and Memory in Rodents; Neuropharmacology (2008) vol. 55, pp. 908-916.
Van Staveren, W. C. G., et al; Cloning and localization of the cGMP-specific Phosphodiesterase Type 9 in the Rat Brain; Journal of Neurocytology (2002) vol. 31, pp. 729-741.
Vippagunta, Sudha, R., et al; Crystalline Solids; Advanced Drug Delivery Reviews (2001) vol. 48, pp. 3-26.
Wang, Huanchen, et al; Insight Into Binding of Phosphodiesterase-9-A Selective Inhibitors by Crystal Structures and Mutagenesis; Journal of Medicinal Chemistry (2009) pp. 1-6.
Wang, Peng., et al; Identification and Characterization of a New Human Type 9 cGMP-specific Phosphodiesterase-Splice Variant (PDE9A5) Different Tissue Distribution and Subcellular Localization of PDE9A Variants; Gene (2003) vol. 314, pp. 15-27.
Weeber, Edwin, et al; Molecular Genetics of Human Cognition; Molecular Interventions (2002) vol. 2, No. 6, pp. 376-391.
Wei, Ji-Ye, et al; Molecular and Pharmacological Analysis of Cyclic Nucloeotide-Gated Channel Function in the Central Nervous System; Progress in Neurobiology (1998) vol. 56, pp. 37-64.
West, Anthony, R; Solid Solutions; Department of Chemistry, Univesity of Aberdeen (1988) vol. 10 3 pages.
Wunder, Frank et al; Characterization of the First Potent and Selective PDE9 Inhibitor Using a cGMP Reporter Cell Line; Molecular Pharmacology (2005) vol. 68, No. 6 pp. 1775-1781.

6-CYCLOALKYL-PYRAZOLOPYRIMIDINONES FOR THE TREATMENT OF CNS DISORDERS

The invention relates to novel pyrazolopyrimidinones according to formula (I)

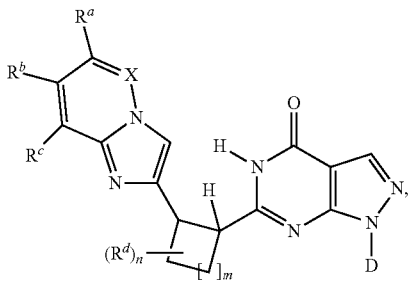

whereby X is $CR^e$ or unsubstituted N, D is optionally substituted cyclopentyl, cyclohexyl, tetrahydrofuranyl, tetrahydropyranyl or 2-, 3- or 4-pyridyl, $R^a$, $R^b$, $R^c$, $R^d$, $R^e$ are either H or optional substituents, m=1 or 2 and n is 0, 1 or 2.

The new compounds are for use as active entities of medicaments or for the manufacture of medicaments, in particular medicaments for the treatment of conditions concerning deficits in perception, concentration, learning or memory. Such conditions may for example be associated with Alzheimer's disease, schizophrenia and other diseases, in particular cognitive impairment associated with such diseases. The compounds of the invention show PDE9 inhibiting properties.

BACKGROUND OF THE INVENTION

The inhibition of phosphodiesterase 9A (PDE9A) is one of the current concepts to find new access paths to the treatment of cognitive impairments due to CNS disorders like Alzheimer's disease, schizophrenia and other diseases or due to any other neurodegenerative process of the brain. With the present invention, new compounds that follow this concept are presented.

Phosphodiesterase 9A is one member of the wide family of phosphodiesterases. These enzymes modulate the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA) and the protein kinase activated by cGMP is called protein kinase G (PKG). Activated PKA and PKG are able in turn to phosphorylate a number of cellular effector proteins (e.g. ion channels, G-protein-coupled receptors, structural proteins, transcription factors). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., Prog. Neurobiol., 1998, 56, 37-64). The phosphodiesterases (PDE) are a control mechanism for the activity of cAMP and cGMP and thus in turn for the corresponding physiological processes. PDEs hydrolyse the cyclic monophosphates to the inactive monophosphates AMP and GMP. Currently, 11 PDE families have been defined on the basis of the sequence homology of the corresponding genes. Individual PDE genes within a family are differentiated by letters (e.g. PDE1A and PDE1B). If different splice variants within a gene also occur, then this is indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nanomolar (nM), PDE9A has high affinity for cGMP. In addition, PDE9A is selective for cGMP (Km for cAMP=230 micromolar (μM)). PDE9A has no cGMP binding domain, suggesting that the enzyme activity is not regulated by cGMP. It was shown in a Western blot analysis that PDE9A is expressed in humans inter alia in testes, brain, small intestine, skeletal muscle, heart, lung, thymus and spleen. The highest expression was found in the brain, small intestine, kidney, prostate, colon and spleen (Fisher et al., J. Biol. Chem., 1998, 273 (25), 15559-15564; Wang et al., Gene, 2003, 314, 15-27). The gene for human PDE9A is located on chromosome 21q22.3 and comprises 21 exons. 4 alternative splice variants of PDE9A have been identified (Guipponi et al., Hum. Genet., 1998, 103, 386-392). Classical PDE inhibitors do not inhibit human PDE9A. Thus, IBMX, dipyridamole, SKF94120, rolipram and vinpocetine show no inhibition on the isolated enzyme in concentrations of up to 100 micromolar (μM). An IC50 of 35 micromolar (μM) has been demonstrated for zaprinast (Fisher et al., J. Biol. Chem., 1998, 273 (25), 15559-15564).

Murine PDE9A was cloned and sequenced in 1998 by Soderling et al. (J. Biol. Chem., 1998, 273 (19), 15553-15558). This has, like the human form, high affinity for cGMP with a Km of 70 nanomolar (nM). Particularly high expression was found in the mouse kidney, brain, lung and liver. Murine PDE9A is not inhibited by IBMX in concentrations below 200 micromolar either; the IC50 for zaprinast is 29 micromolar (Soderling et al., J. Biol. Chem., 1998, 273 (19), 15553-15558). It has been found that PDE9A is strongly expressed in some regions of the rat brain. These include olfactory bulb, hippocampus, cortex, basal ganglia and basal forebrain (Andreeva et al., J. Neurosci., 2001, 21 (22), 9068-9076). The hippocampus, cortex and basal forebrain in particular play an important role in learning and memory processes. As already mentioned above, PDE9A is distinguished by having particularly high affinity for cGMP. PDE9A is therefore active even at low physiological concentrations, in contrast to PDE2A (Km=10 micromolar (μM); Martins et al., J. Biol. Chem., 1982, 257, 1973-1979), PDE5A (Km=4 micromolar (μM); Francis et al., J. Biol. Chem., 1980, 255, 620-626), PDE6A (Km=17 micromolar (μM); Gillespie and Beavo, J. Biol. Chem., 1988, 263 (17), 8133-8141) and PDE11A (Km=0.52 micromolar (μM); Fawcett et al., Proc. Nat. Acad. Sci., 2000, 97 (7), 3702-3707). In contrast to PDE2A (Murashima et al., Biochemistry, 1990, 29, 5285-5292), the catalytic activity of PDE9A is not increased by cGMP because it has no GAF domain (cGMP-binding domain via which the PDE activity is allosterically increased) (Beavo et al., Current Opinion in Cell Biology, 2000, 12, 174-179). PDE9A inhibitors may therefore lead to an increase in the baseline cGMP concentration.

This outline will make it evident that PDE9A engages in specific physiological processes in a characteristic and unique manner, which distinguishes the role of PDE9A from any of the other PDE family members.

WO 2004/099210 discloses 6-arylmethyl-substituted pyrazolopyrimidinones which are PDE9 inhibitors.

WO 2004/099211 discloses 6-cyclylmethyl- and 6-alkylmethyl-substituted pyrazolopyrimidines and their use for the improvement of cognition, concentration etc.

DE 102 38 722 discloses the use of PDE9A-inhibitors for the improvement of cognition, concentration.

WO 2004/018474 discloses phenyl-substituted pyrazolopyrimidines and their use for the improvement of perception, concentration learning and/or memory.

WO 2004/026876 discloses alkyl-substituted pyrazolopyrimidines and their use for the improvement of awareness, concentration learning capacity and/or memory performance.

WO 2004/096811 discloses heterocyclic bicycles as PDE9 inhibitors for the treatment of diabetes, including type 1 and type 2 diabetes, hyperglycemia, dyslipidemia, impaired glucose tolerance, metabolic syndrome and/or cardiovascular disease.

WO2009068617 discloses PDE9 inhibiting compounds derived from pyrazolopyrimidinones with a substituted phenylmethyl- or pyridyl-methyl group in the 6-position.

WO2010112437 discloses PDE9 inhibiting compounds derived from pyrazolopyrimidinones with a phenyl or heteroaryl substituted arylmethyl- or heteroaryl-methyl group in the 6-position.

WO 2009/121919 discloses PDE9 inhibitors derived from pyrazolopyrimidinones with a non-aromatic heterocyclyl group in the 1-position, among which is tetrahydropyranyl.

WO 2010/026214 discloses PDE9 inhibitors derived from pyrazolopyrimidinones with a cycloalkyl or a cycloalkenyl group in the 1-position, among which is 4,4-difluorocyclohexyl.

Some references are directed to nucleoside derivatives. For example, WO 2002/057425 discloses nucleoside derivatives which are inhibitors of RNA-dependent RNA viral polymerase. WO 2001/060315 discloses nucleoside derivatives for the treatment of hepatitis C infection. EP679657 discloses compounds that serve as ribonucleoside analogues. US2002058635 discloses purine L-nucleoside compounds, in which both the purine rings and the carbohydrate ring (pentose ring) are either modified, functionalized, or both, so the carbohydrate ring for example must show at least one esterified hydroxy group.

WO 2005/051944 discloses oxetane-containing nucleosides for the treatment of nucleoside analogue related disorders such as disorders involving cellular proliferation and infection.

WO 2006/084281 discloses inhibitors of the E1 activation enzyme that have a sulfonamide moiety.

WO 1998/40384 discloses pyrazolopyrimidinones which are PDE1, 2 and 5 inhibitors and can be employed for the treatment of cardiovascular and cerebrovascular disorders and disorders of the urogenital system.

CH396 924, CH396 925, CH396 926, CH396 927, DE1147234 and DE1149013, describe pyrazolopyrimidines which have a coronary-dilating effect and which can be employed for the treatment of disturbances of myocardial blood flow.

U.S. Pat. No. 3,732,225 describes pyrazolopyrimidines which have an anti-inflammatory and blood glucose-lowering effect.

DE2408906 describes styrylpyrazolopyrimidinones which can be employed as antimicrobial and anti-inflammatory agents for the treatment of, for example, oedema.

OBJECTIVE OF THE INVENTION

Changes in the substitution pattern of pyrazolopyrimidinones result in interesting changes concerning biological activity and changes in the affinity towards different target enzymes.

Therefore it is an objective of the present invention to provide compounds as herein described, in particular in the claims, that effectively modulate PDE9A for the purpose of the development of a medicament, in particular in view of diseases or conditions, the treatment of which are accessible via PDE9A modulation.

It is another objective of the present invention to provide compounds that are useful for the manufacture of a medicament for the treatment of CNS disorders.

Yet another objective of the present invention is to provide compounds which show a favourable safety profile.

Another objective of the present invention is to provide compounds that have a favourable selectively profile in favour for PDE9A inhibition over other PDE family members and other pharmacological targets and by this may provide advantage.

Yet another objective is to provide a medicament that may not only serve for treatment but might also be used for the prevention or modification of the corresponding disease or condition.

The present invention further provides a pharmaceutical composition comprising a compound as herein described, in particular in the claims, and a pharmaceutically acceptable carrier.

The present invention further provides a method for the treatment of any of the conditions as described herein in a mammal in need of such treatment, preferably a human, comprising administering to the mammal a therapeutically effective amount of a compound as herein described, in particular in the claims.

The present invention further provides a compound as herein described, in particular in the claims, for use in a method of treatment of the human or animal body by therapy.

DETAILED DESCRIPTION OF THE PRESENT INVENTION

The compounds of the present invention are characterised by general formula (I):

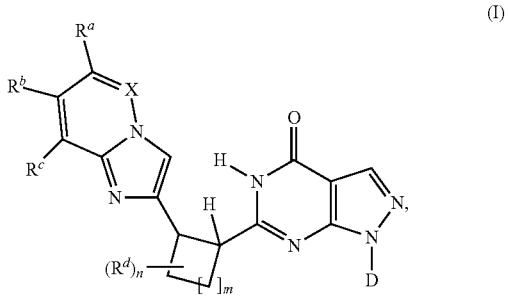

wherein
X is N or $CR^e$,
$R^a$, $R^b$, $R^c$, $R^e$ are selected independently of each other from the group consisting of H, $C_{1-6}$-alkyl-, $C_{1-6}$-alkyl-O—, $CF_3$—, $CHF_2$—, $CH_2F$—, NC— and halogen;
   whereby $C_{1-6}$-alkyl- and $C_{1-6}$-alkyl-O— optionally may be substituted with haolgen, preferably with fluoro
$R^d$: is selected from the group consisting of fluorine, NC—, —$CF_3$, —$CHF_2$, —$CH_2F$, and methyl;
D: is selected from the group consisting of cyclopentyl, cyclohexyl, tetrahydrofuranyl, tetrahydropyranyl, 2-, 3- and 4-pyridyl, whereby cyclopentyl and cyclohexyl optionally may be substituted by 1 or 2 substituents, whereby said substituents may be selected independently of one another from the group consisting of fluorine, NC—, $F_3C$—, $HF_2C$— and $FH_2C$—;

whereby tetrahydrofuranyl and tetrahydropyranyl optionally may be substituted by 1 or 2 substituents, whereby said substituents may be selected independently of one another from the group consisting of fluorine, NC—, $F_3C$—, $HF_2C$— and $FH_2C$—;

whereby pyridyl optionally may be substituted by 1, 2, 3 or 4 substituents, whereby said substituents may be selected independently of one another from the group consisting of fluorine, chlorine, bromine, NC—, $F_3C$—, $HF_2C$—, $FH_2C$—, $F_3C$—$CH_2$—, $C_{1-6}$-alkyl- and $C_{3-7}$-cycloalkyl;

m: is selected from 1 or 2, preferably 1;
n: is selected from 0, 1 or 2, preferably, 0 or 1, more preferably 0,
  whereby if n=2, the two groups $R^d$ are selected independently of one another;
and salts, preferably pharmaceutically acceptable salts thereof, solvates thereof and the solvates of the aforementioned salts thereof.

This embodiment is embodiment 1 of the present invention.

Embodiment 2 of the Present Invention

Another embodiment of the invention concerns a compound according to general formula (I), wherein
X is N or $CR^e$,
$R^a$, $R^b$, $R^c$, $R^e$ are selected independently of each other from the group consisting of H, $C_{1-3}$-alkyl-, $C_{1-3}$-alkyl-O—, —$CF_3$, —$CHF_2$, —$CH_2F$, NC— and halogen;
  whereby $C_{1-6}$-alkyl- and $C_{1-6}$-alkyl-O— optionally may be substituted with halogen, preferably fluoro
$R^d$: is selected from the group consisting of fluorine, NC—, —$CF_3$, —$CHF_2$, —$CH_2F$ and methyl;
D: is selected from the group consisting of cyclopentyl, cyclohexyl, tetrahydrofuranyl, tetrahydropyranyl, 2-, 3- and 4-pyridyl,
  whereby cyclopentyl and cyclohexyl optionally may be substituted by 1 or 2 substituents, whereby said substituents may be selected independently of one another from the group consisting of fluorine, $F_3C$—, $HF_2C$— and $FH_2C$—;
  whereby tetrahydrofuranyl and tetrahydropyranyl optionally may be substituted by 1 or 2 substituents, whereby said substituents may be selected independently of one another from the group consisting of fluorine, $F_3C$—, $HF_2C$— and $FH_2C$—;
  whereby pyridyl optionally may be substituted by 1, 2, 3 or 4, preferably 1, 2 or 3, more preferably 1 or 2, substituents, whereby said substituents may be selected independently of one another from the group consisting of fluorine, chlorine, bromine, NC—, $F_3C$—, $HF_2C$—, $FH_2C$—, $F_3C$—$CH_2$—, $C_{1-6}$-alkyl- and $C_{3-7}$-cycloalkyl;
m: is selected from 1 or 2, preferably m is 1;
n: is 0, 1 or 2, preferably n is 0 or 1, more preferably n is 0,
  whereby if n=2, these two groups $R^d$ are selected independently of one another;
and salts, preferably pharmaceutically acceptable salts thereof, solvates thereof and the solvates of the aforementioned salts thereof.

Embodiment 3 of the Present Invention

Another embodiment of the invention concerns a compound according to general formula (I), wherein
X is N or $CR^e$,
$R^a$, $R^b$, $R^c$, $R^e$ are selected independently of each other from the group consisting of H, methyl, ethyl, methoxy, ethoxy, —$CF_3$, —$CHF_2$, —$CH_2F$, NC— and halogen; preferably $R^a$, $R^b$, $R^c$, $R^e$ are selected independently from the group consisting of H, methyl, ethyl, methoxy, ethoxy, —$CF_3$ and NC—,
D: is selected from the group consisting of cyclopentyl, cyclohexyl, tetrahydrofuranyl, tetrahydropyranyl, 2-, 3- and 4-pyridyl,
  whereby cyclopentyl and cyclohexyl optionally may be substituted by 1 or 2 substituents, whereby said substituents may be selected independently of one another from the group consisting of fluorine, $F_3C$—, $HF_2C$— and $FH_2C$—;
  whereby tetrahydrofuranyl and tetrahydropyranyl optionally may be substituted by 1 or 2 substituents, whereby said substituents may be selected independently of one another from the group consisting of fluorine, $F_3C$—, $HF_2C$— and $FH_2C$—;
  whereby pyridyl optionally may be substituted by 1, 2, 3 or 4, preferably 1, 2 or 3, more preferably 1 or 2, substituents, whereby said substituents may be selected independently of one another from the group consisting of fluorine, chlorine, bromine, NC—, $F_3C$—, $HF_2C$—, $FH_2C$—, $F_3C$—$CH_2$—, $C_{1-6}$-alkyl- and $C_{3-7}$-cycloalkyl;
m: is selected from 1 or 2, preferably m is 1;
n is 0,
and salts, preferably pharmaceutically acceptable salts thereof, solvates thereof and the solvates of the aforementioned salts thereof.

Embodiment 4 of the Present Invention

Another embodiment of the invention concerns a compound according to general formula (I), wherein
X is N or $CR^e$,
$R^b$, $R^c$, $R^d$, $R^e$ are each H,
$R_a$ is selected from the group consisting of H, methyl, ethyl, methoxy, ethoxy, —$CF_3$, —$CHF_2$, —$CH_2F$ and F;
D: is selected from the group consisting of cyclopentyl, cyclohexyl, tetrahydrofuranyl, tetrahydropyranyl, 2-, 3- and 4-pyridyl,
  whereby cyclopentyl and cyclohexyl optionally may be substituted by 1 or 2 substituents, whereby said substituents may be selected independently of one another from the group consisting of fluorine, $F_3C$—, $HF_2C$— and $FH_2C$—;
  whereby tetrahydrofuranyl and tetrahydropyranyl optionally may be substituted by 1 or 2 substituents, whereby said substituents may be selected independently of one another from the group consisting of fluorine, $F_3C$—, $HF_2C$— and $FH_2C$—;
  whereby pyridyl optionally may be substituted by 1, 2, 3 or 4, preferably 1, 2 or 3, more preferably 1 or 2, substituents, whereby said substituents may be selected independently of one another from the group consisting of fluorine, chlorine, bromine, NC—, $F_3C$—, $HF_2C$—, $FH_2C$—, $F_3C$—$CH_2$—, $C_{1-6}$-alkyl- and $C_{3-7}$-cycloalkyl;
m: is selected from 1 or 2, preferably m is 1;
n is 0, and salts, preferably pharmaceutically acceptable salts thereof, solvates thereof and the solvates of the aforementioned salts thereof.

Embodiments 5 to 9 of the Present Invention

Other embodiments of the invention concern a compound according to each of embodiments 1 to 4, wherein m is 1,
and salts, preferably pharmaceutically acceptable salts thereof, solvates thereof and the solvates of the aforementioned salts thereof.

Embodiments 10 to 18 of the Present Invention

Other embodiments of the invention concern a compound according to each of embodiments 1 to 9, wherein
D is either 4,4-difluorocyclohexyl or tetrahydropyran-4-yl or 4-methyl-3-pyridyl and none of these two groups has further substituents and
m is 1.
and salts, preferably pharmaceutically acceptable salts thereof, solvates thereof and the solvates of the aforementioned salts thereof.

Embodiments 19 to 36 of the present invention concern a compound according to each of embodiments 1 to 18, wherein X=N.

Embodiments 37 to 56 of the present invention concern a compound according to each of embodiments 1 to 18, wherein $X=CR^e$.

For all embodiments 1 to 56: the configuration of the cycloalkl group at position 6 of the pyrazolopyrimidinones group with respect to said pyrazolopyrimidinones group and the substituent $R^1$ may be cis or trans.

In this respect the compounds of the invention may have the following configurations:

trans configuration 1                                    formula (Ia)

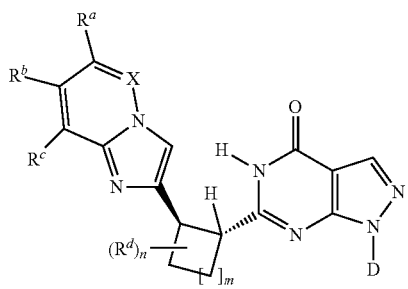

trans configuration 2                                    formula (Ib)

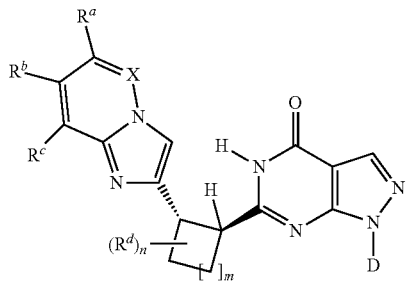

cis configuration 1                                      formula (Ic)

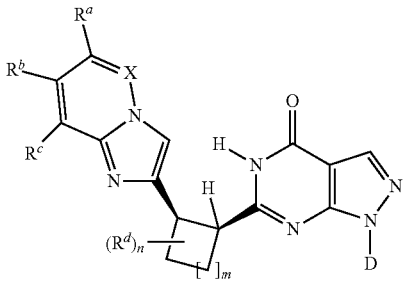

cis configuration 2                                      formula (Id)

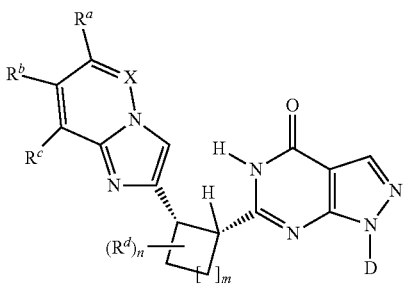

whereby $R^a, R^b, R^c, R^d$, D, m and n are as defined in any of the embodiments 1 to 56. m. These stereochemically defined embodiments are a further aspect of the invention.

Embodiment 57 of the Present Invention

Within the context of the present invention one or more compound(s) is (are) preferred that are selected from the group of specifically defined species as listed in the following table 1. These compounds represent compounds according to general formula (I) wherein X is N. The left column contains a letter code to identify the compound family, which is the group of compounds that have the same general chemical structural formula if no stereochemical properties are considered.

| Table 1 of species: | |
|---|---|
| A | 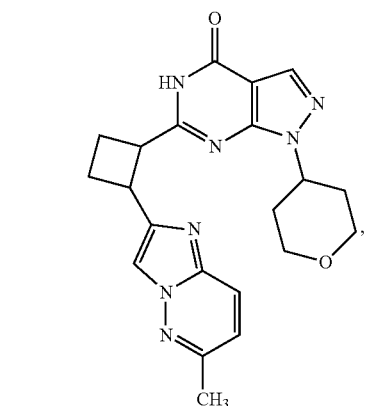 |
| | Compound family A |

Table 1 of species:
A a
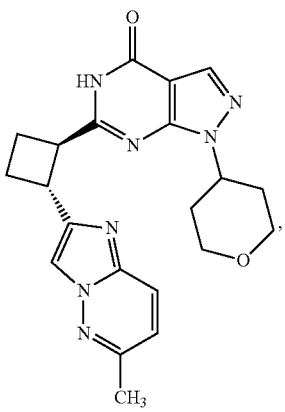 [SMILES: Cc1ccc2nc([C@@H]3CC[C@H]3c3nc4c(cnn4C4CCOCC4)c(=O)[nH]3)cn2n1]
A b
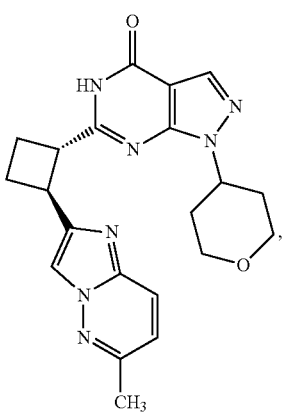 [SMILES: Cc1ccc2nc([C@H]3CC[C@@H]3c3nc4c(cnn4C4CCOCC4)c(=O)[nH]3)cn2n1]
A c
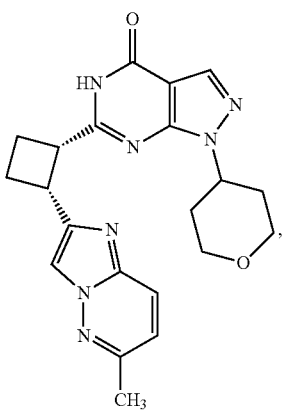 [SMILES: Cc1ccc2nc([C@@H]3CC[C@@H]3c3nc4c(cnn4C4CCOCC4)c(=O)[nH]3)cn2n1]
Table 1 of species:
A d
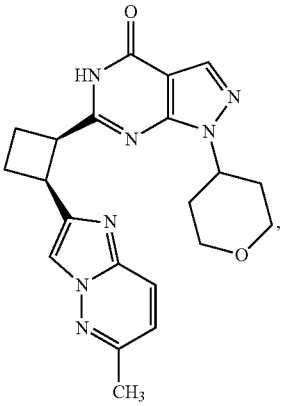 [SMILES: Cc1ccc2nc([C@H]3CC[C@H]3c3nc4c(cnn4C4CCOCC4)c(=O)[nH]3)cn2n1]
B
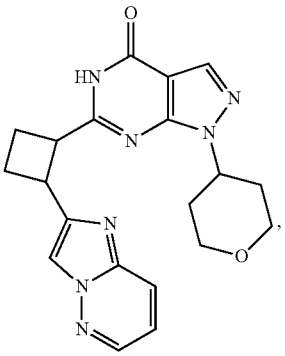 [SMILES: O=c1[nH]c([C@H]2CC[C@H]2c2cn3ncccc3n2)nc2c1cnn2C1CCOCC1]
Compound family B
B a
B b
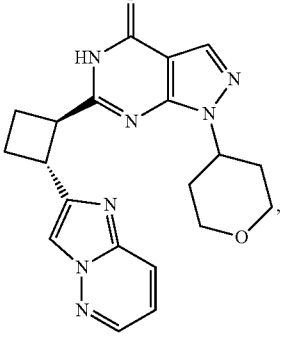

Table 1 of species:

B
c

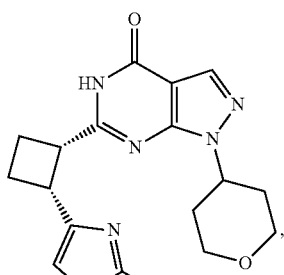

B
d

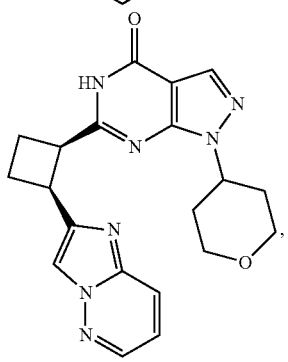

and salts, preferably pharmaceutically acceptable salts thereof, solvates thereof and the solvates of the aforementioned salts thereof.

Embodiment 58 of the Present Invention

Another embodiment of the present invention concerns one or more compound(s) is (are) that are selected from the group of specifically defined species as listed in the following table 2. These compounds represent compounds according to general formula (I) wherein X is $CR^e$ and $R^e$ is H. The left column contains a letter code to identify the compound family, which is the group of compounds that have the same general chemical structural formula if no stereochemical properties are considered.

Table 2 of species:

C

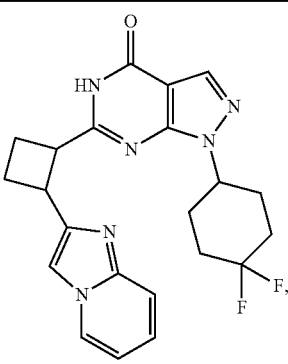

Compound family C

Table 2 of species:

C
a

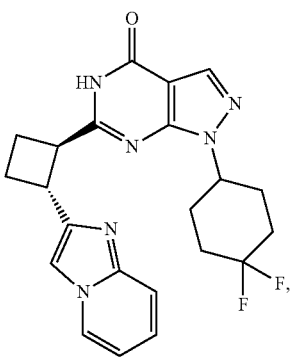 [SMILES: O=c1[nH]c([C@@H]2CC[C@H]2c2cn3ccccc3n2)nc2c1cnn2C1CCC(F)(F)CC1]

C
b

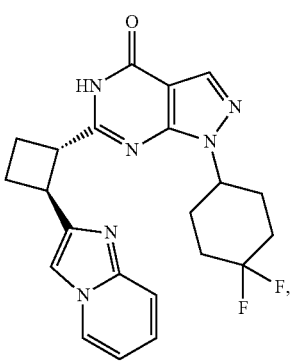 [SMILES: O=c1[nH]c([C@H]2CC[C@@H]2c2cn3ccccc3n2)nc2c1cnn2C1CCC(F)(F)CC1]

C
c

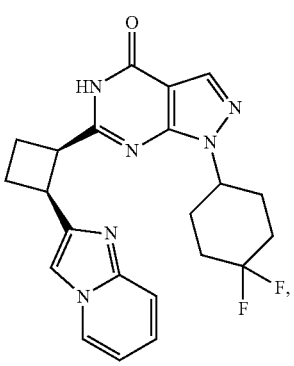 [SMILES: O=c1[nH]c([C@@H]2CC[C@@H]2c2cn3ccccc3n2)nc2c1cnn2C1CCC(F)(F)CC1]

C
d

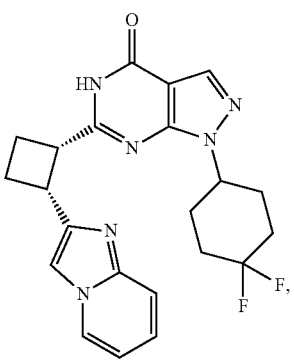 [SMILES: O=c1[nH]c([C@H]2CC[C@H]2c2cn3ccccc3n2)nc2c1cnn2C1CCC(F)(F)CC1]

Table 2 of species:

| D | |
|---|---|
| D | 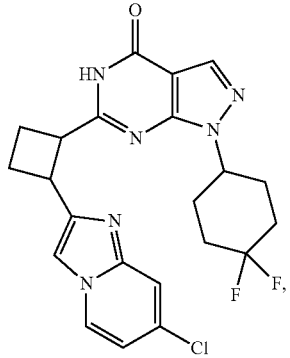<br>Compound family D |
| Da | 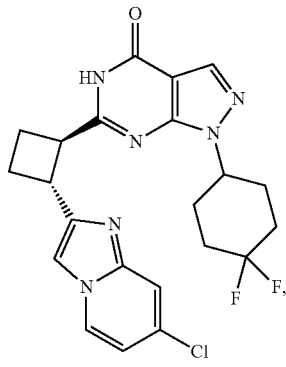 [SMILES: O=c1[nH]c([C@@H]2CC[C@H]2c2cn3ccc(Cl)cc3n2)nc2c1cnn2C1CCC(F)(F)CC1] |
| Db | 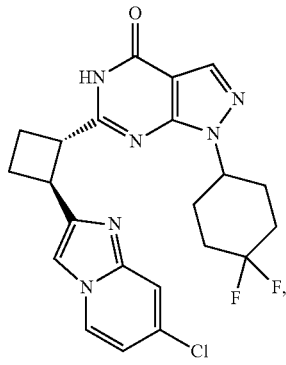 [SMILES: O=c1[nH]c([C@H]2CC[C@@H]2c2cn3ccc(Cl)cc3n2)nc2c1cnn2C1CCC(F)(F)CC1] |
| Dc | 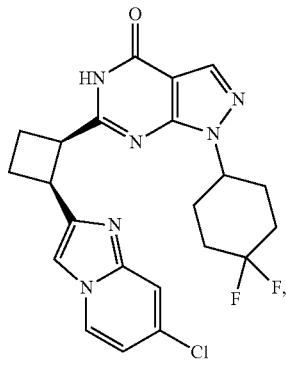 [SMILES: O=c1[nH]c([C@@H]2CC[C@@H]2c2cn3ccc(Cl)cc3n2)nc2c1cnn2C1CCC(F)(F)CC1] |
| Dd | 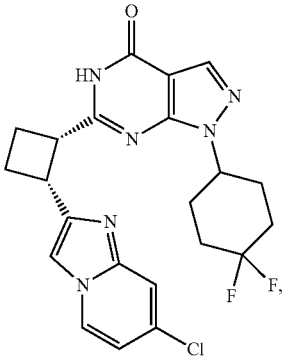 [SMILES: O=c1[nH]c([C@H]2CC[C@H]2c2cn3ccc(Cl)cc3n2)nc2c1cnn2C1CCC(F)(F)CC1] | and salts, preferably pharmaceutically acceptable salts thereof, solvates thereof and the solvates of the aforementioned salts thereof.

Within the latter group of compounds according to tables 1 and 2 (i.e. embodiments 57 and 58), compounds that show trans configuration with respect to the substitution at the cyclobutyl-group may be preferred over compounds with cis configuration. Of the possible trans configured compounds one may show advantages in efficacy. The more efficacious a compound, the more it is among the preferred compounds. Other criterion which may differentiate preferred compounds according to the invention are the balance of efficacy and safety, and selectivity vs. other PDE family members such as PDE1C.

The different stereoisomers are subject to individual embodiments according to the invention: For each of the embodiments 1 to 56: whenever D may be tetrahydrofuranyl, it is preferably tetrahydrofuran-3-yl; whenever D may be tetrahydropyranyl it is preferable tetrahydropyran-3-yl or tetrahydropyran-4-yl, more preferably tetrahydropyran-4-yl.

TERMS AND DEFINITIONS

Terms not specifically defined herein should be given the meanings that would be given to them by a person skilled in the art in light of the disclosure and the context. Examples include that specific substituents or atoms are presented with their 1 or 2 letter code, like H for hydrogen, N for nitrogen, C for carbon, O for oxygen, S for sulphur and the like. Optionally but not mandatory the letter is followed or preceeded by a hyphen to indicate a bond. As used in the specification, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or alkyl radical having 1 to 6 carbon atoms. In general, for groups comprising two or more subgroups, the last named group is the radical attachment point, for example, "alkyl-O—" means a monovalent radical of the formula alkyl-O—, which is attached via the oxygen atom thereof (i.e. a alkoxy-substituent). If the term of a substituent starts or ends with a minus sign or hyphen, i.e.—, this sign emphasises the attachment point like in the aforementioned example Alkyl-O—, where the O is linked to the group of which the alkoxy-group is a substituent. Unless otherwise specified below, conventional definitions of terms control and conventional stable atom valences are presumed and achieved in all formulas and groups.

In general, if terms are specifically defined with a given context, such specific definitions shall prevail over the more general definitions as outlined in this paragraph.

In general, all "tautomeric forms and isomeric forms and mixtures", whether individual geometric isomers or optical isomers or racemic or non-racemic mixtures of isomers of a chemical structure or compound are intended, unless the specific stereochemistry or isomeric form is specifically indicated in the compound name or structure. Specific definitions prevail.

"Substitution": The term "substituted" as used herein explicitly or implicitly, means that any one or more hydrogen(s) on the designated atom is replaced with a member of the indicated group of substituents, provided that the designated atom's normal valence is not exceeded. In case a substituent is bound via a double bond, e.g. an oxo substituent, such substituent replaces two hydrogen atoms on the designated atom. The substitution shall result in a stable compound. "Stable" in this context preferably means a compound that from a pharmaceutical point of view is chemically and physically sufficiently stable in order to be used as an active pharmaceutical ingredient of a pharmaceutical composition. If a substituent is not defined, it shall be hydrogen. By the term "optionally substituted" is meant that either the corresponding group is substituted or it is not. A characterisation that substituents of the same group may be "selected independently of one another" shall mean that the corresponding substituents may be the same or may be different.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"pharmaceutically acceptable salt(s)" of the compounds according to the invention are subject of the present invention as well. The term "pharmaceutically acceptable salt(s)" refers to derivatives of the disclosed compounds wherein the parent compound is modified by making acid or base salts thereof, preferably addition salts. Examples of pharmaceutically acceptable salts include, but are not limited to, mineral or organic acid salts of basic residues/parts of the compounds of the present invention such as aminofunctions; acidic residues/parts within compounds of the present invention may form salts with alkali or organic bases. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid, hydrobromic acid, sulfuric acid, sulfamic acid, phosphoric acid, nitric acid and the like; and the salts prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid and the like.

Physiologically acceptable salts with bases also may include salts with conventional bases such as, by way of example and preferably, alkali metal salts (e.g. sodium and potassium salts), alkaline earth metal salts (e.g. calcium and magnesium salts) and ammonia, organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, dehydroabietylamine, arginine, lysine, ethylenediamine and methylpiperidine and the like.

The pharmaceutically acceptable salts of the present invention can be synthesized from the parent compound with basic or acidic properties by conventional chemical methods. Generally, such salts can be prepared by reacting the free acid or base form of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

A "Prodrug" is considered a compound that is designed to release a biologically active compound according to the present invention in-vivo when such prodrug is administered to a mammalian subject. Prodrugs of compounds according to the present invention are prepared by modifying functional groups present in the compound of the invention in such a way that these modifications are retransformed to the original functional groups under physiological conditions. It will be appreciated that prodrugs of the compounds according to the present inventions are subject to the present invention as well.

"Metabolites" are considered derivatives of the compounds according to the present invention that are formed in-vivo. Active metabolites are such metabolites that cause a pharmacological effect. It will be appreciated that metabolites of the compounds according to the present inventions are subject to the present invention as well, in particular active metabolites.

Some of the compounds may form "solvates". For the purposes of the invention the term "solvates" refers to those forms of the compounds which form, in the solid or liquid state, a complex by coordination with solvent molecules. Hydrates are a specific form of solvates in which the coordination takes place with water. According to the present invention, the term preferably is used for solid solvates, such as amorphous or more preferably crystalline solvates.

"Scaffold": The scaffold of the compounds according to the present invention is represented by the following core structure. The numeration of the positions of the ring member atoms is indicated in bold:

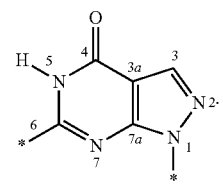 [SMILES: *c1nc2c(cnn2*)c(=O)[nH]1]

It will be evident for the skilled person in the art, that this scaffold can be described by its tautomeric "enol" form

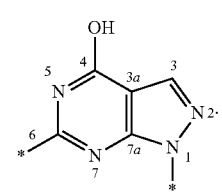

In the context of the present invention both structural representations of the scaffold shall be considered the subject of the present invention, even if only one of the two representatives is presented. Without meant to be limiting or bound, it is believed that for the majority of compounds under ambient conditions and therewith under conditions which are the relevant conditions for a pharmaceutical composition comprising said compounds, the equilibrium of the tautomeric forms lies on the side of the pyrazolopyrimdin-4-one representation. Therefore, all embodiments are presented as pyrazolopyrimdin-4-one-derivatives or more precisely as pyrazolo[3,4-d]pyrimidin-4-one derivatives.

"Bonds": If within a chemical formula of a ring system or a defined group a substituent is directly linked to an atom or a group like "RyR" in the formula below, this shall mean that the substituent is only attached to the corresponding atom. If however from another substituent like "RxR" a bond is not specifically linked to an atom of the ring system but drawn towards the centre of the ring or group this means that this substituent "RxR" may be linked to any meaningful atom of the ring system/group unless stated otherwise.

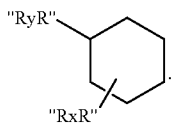

The bond symbol "–" (=minus sign) or the symbol "–*" (=minus sign followed by an asterisk sign) stands for the bond through which a substituent is bound to the corresponding remaining part of the molecule/scaffold. In cases in that the minus sign does not seem to be sufficiently clear, there may be added an asterisk to the bond symbol "-" in order to determine the point of attachment of said bond with the corresponding main part of the molecule/scaffold.

The term "$C_{1-6}$-alkyl" denotes a saturated, branched or unbranched hydrocarbon group with 1 to 6 C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl. This definition applies for the use of "alkyl" in any reasonable context within the present description in the absence of a further definition.

The term "$C_{3-7}$-cycloalkyl" denotes a saturated monocyclic group with 3 to 7 C ring atoms. Preferred are 5 or 6 membered cycloalkyl-groups. There are no other ring atoms than carbon atoms. Examples of such groups include cyclopropyl, cyclobutyl, cyclopentyl, cyclohexyl, cycloheptyl. This definition applies for "cycloalkyl" in any reasonable context within the present description in the absence of a further definition.

The terms "halogen" stands for fluoro (F), chloro (Cl) and bromo (Br) substituents, preferably F and Cl and more preferably F.

The terms "pyridyl" defines a pyridine-substituent, sometimes also called pyridinyl.

Expressions like "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis. Thus the expression "prevention of a disease" as used herein means the management and care of an individual at risk of developing the disease prior to the clinical onset of the disease. The purpose of prevention is to combat the development of the disease, condition or disorder and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" preferably means therapeutic treatment of (e.g. preferably human) patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition, disorder or a symptom thereof. Treatment includes the administration of the active compounds to eliminate or control the disease, condition or disorder as well as to alleviate the symptoms or complications associated with the disease, condition or disorder.

The following schemes shall illustrate generally how to manufacture the compounds of the present invention by way of example. The abbreviated substituents may be as defined for the embodiments of formula (I) if not defined otherwise within the context of the schemes:

Scheme 1

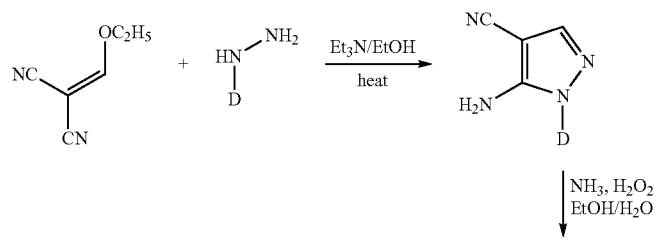

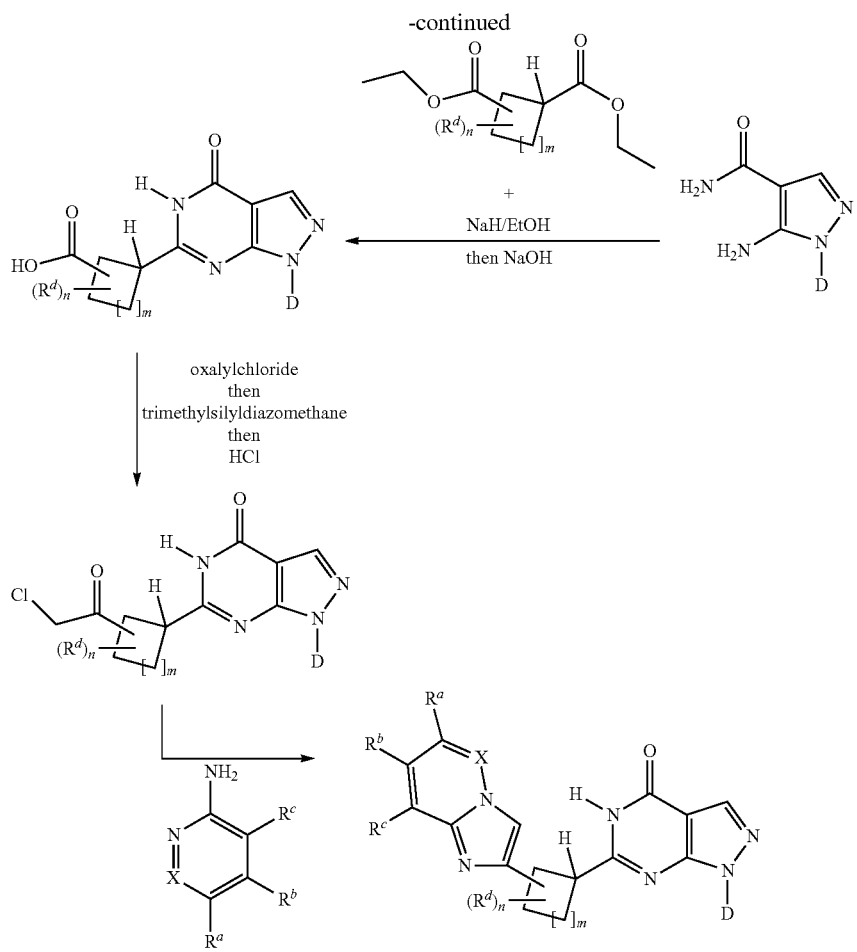

Scheme 1:

In a first step 2-ethoxymethylene-malononitrile is condensed with mono-substituted hydrazines by heating in an appropriate solvent like ethanol in the presence of a base (e.g. triethylamine) to form the corresponding 5-amino-1H-pyrazole-4-carbonitriles. These compounds are converted in a second step to the corresponding amides, e.g. by treatment of an ethanolic solution with ammonia (25% in water) and hydrogen peroxide (35% in water). In a third step, heating with dicarboxylic acid diesters under basic conditions (e.g. sodium hydride in ethanol) followed by the addition of aqueous sodium hydroxide leads to 4-oxo-4,5-dihydro-1H-pyrazolo[3,4-d]pyrimidin-6-yl substituted carboxylic acids. Successive reaction with oxalylchloride, trimethylsilyldiazomethane and hydrochloric acid, followed by reaction with the corresponding 2-aminopyridazine(s), or the corresponding 2-amino-pyridine(s) respectively, leads to the final product(s).

Scheme 2

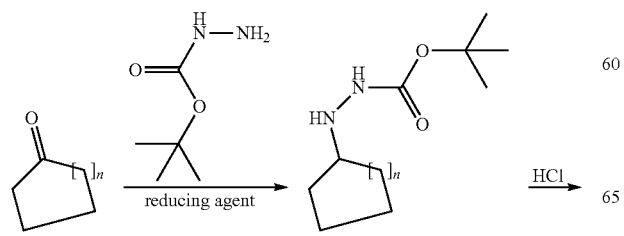

-continued

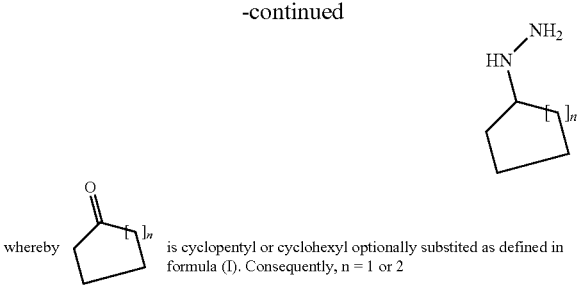

whereby is cyclopentyl or cyclohexyl optionally substited as defined in formula (I). Consequently, n = 1 or 2

Scheme 2:

The mono-substituted hydrazine derivatives, that are used in step 1 of scheme 1 can be prepared by reductive amination of a ketone with hydrazinecarboxylic acid tert-butyl ester followed by a deprotection step as shown in scheme 4 for an D being cyclopentyl or cyclohexyl as defined in general formula (I) [cf., for example, J. W. Timberlake et al., "Chemistry of Hydrazo-, Azo-and Azoxy Groups"; Patai, S., Ed.; 1975, Chapter 4; S. C. Hung et al., Journal of Organic Chemistry 1981, 46, 5413-5414].

Further information also can be found in:
WO 2004/099210 (in particular page 9, last paragraph to page 14, line 8, incorporated by reference),
with respect to the general manufacture of compounds with D being tetrahydropyranyl more information can be found in WO2009/121919, particularly on page 120 to 125 and the experimental part thereof (herewith incorporated by reference), with respect to D being 4,4-difluorocyclohexyl more information can be found in WO 2010/026214, particularly on page 59 to 63 and the experimental part thereof (herewith incorporated by reference),
and in the experimental section (exemplary embodiments) of this description.

Method of Treatment

The present invention refers to compounds, which are considered effective in the treatment of diseases. The compounds according to the invention effectively inhibit phosphodiesterase 9A and show preference in for PDE9A compared with other PDE family members. Therefore the compounds are effective and selective inhibitors of PDE9A and can be used for the development of medicaments. Such medicaments shall preferably be used for the treatment of diseases in which the inhibition of PDE9A can result in a therapeutic, prophylactic or disease modifying effect. Preferably the medicaments shall be used to improve perception, concentration, cognition, learning or memory, in particular in situations/diseases/syndromes such as:

mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Picks syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, schizophrenia, schizophrenia (with dementia), Korsakoff s psychosis or cognitive impairment associated with depression or bipolar disorder.

Another aspect of the present invention concerns the treatment of a disease which is accessible by PDE9A modulation, in particular sleep disorders like insomnia or narcolepsy, bipolar disorder, metabolic syndrome, obesity, diabetes mellitus, including type 1 or type 2 diabetes, hyperglycemia, dyslipidemia, impaired glucose tolerance, or a disease of the testes, brain, small intestine, skeletal muscle, heart, lung, thymus or spleen.

Thus the medical aspect of the present invention can be summarised in that it is considered that a compound according to formula (I) or (II) as herein defined, in particular the specifically defined species compounds is used as a medicament.

Such a medicament preferably is for the treatment of a CNS disease.

In an alternative use, the medicament is for the treatment of a CNS disease, the treatment of which is accessible by the inhibition of PDE9.

In an alternative use, the medicament is for the treatment of a disease that is accessible by the inhibition of PDE9, specifically PDE9A.

In an alternative use, the medicament is for the treatment, amelioration and/or prevention of cognitive impairment being related to perception, concentration, cognition, learning or memory, preferably if such congitive impairment is associated with a disease or condition as described in this section.

In an alternative use, the medicament is for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Picks syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, schizophrenia (with dementia), Korsakoff's psychosis or cognitive impairment associated with depression or bipolar disorder.

In an alternative use, the medicament is for the treatment of Alzheimer's disease, schizophrenia or cognitive impairemnt associated with Alzheimers's disease or associated with schizophrenia.

In an alternative use, the medicament is for the treatment of sleep disorders, bipolar disorder, metabolic syndrome, obesity, diabetes mellitus, hyperglycemia, dyslipidemia, impaired glucose tolerance, or a disease of the testes, brain, small intestine, skeletal muscle, heart, lung, thymus or spleen.

In a further aspect of the invention, the present invention relates to the method of treatment or prevention of a condition or disease selected from the above listed groups of conditions and diseases, whereby the method comprises the administration of a therapeutically effective amount of a compound according to the invention in a human being in need thereof.

Pharmaceutical Compositions

Medicaments for administration, which are also subject to the present invention, comprise a compound according to the present invention in a therapeutically effective amount and a pharmaceutical carrier. By "therapeutically effective amount" it is meant that if the medicament is applied via the appropriate regimen adapted to the patient's condition, the amount of said compound of formula (I) will be sufficient to effectively treat, to prevent or to decelerate the progression of the corresponding disease, or otherwise to ameliorate the state of a patient suffering from such a disease. It may be the case that the "therapeutically effective amount" in a monotherapy will differ from the "therapeutically effective amount" in a combination therapy with another medicament.

The dose range of the compounds of general formula (I) applicable per day may be usually from 0.1 to 5000 mg, preferably from 0.1 to 1000 mg, preferably from 2 to 500 mg, more preferably from 5 to 250 mg, most preferably from 10 to 100 mg. A dosage unit (e.g. a tablet) preferably may contain between 2 and 250 mg, particularly preferably between 10 and 100 mg of the compounds according to the invention.

The actual pharmaceutically effective amount or therapeutic dosage will depend on factors known by those skilled in the art such as age, weight, gender or other condition of the patient, route of administration, severity of disease and the like.

The compounds according to the invention may be administered by oral, parenteral (intravenous, intramuscular etc.), intranasal, sublingual, inhalative, intrathecal, topical or rectal route. Suitable preparations for administering the compounds according to the present invention include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions may be prepared in the usual way, e.g. with the addition of isotonic agents, preservatives such as p-hydroxybenzoates or stabilisers such as alkali metal salts of ethylenediamine-tetra-acetic acid, optionally using emulsifiers and/or dispersants, while if water shall be used as diluent, for example, organic solvents may optionally be used as solubilisers or dissolving aids and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated.

Combinations with Other Active Substances

In another aspect, the present invention relates to a combination therapy in which a compound according to the present invention is administered together with another active compound. Accordingly, the invention also refers to pharmaceutical formulations that provide such a combination of active ingredients, whereby one of which is a compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the compounds of the present invention, preferably at least one compound according to the present invention, with another active compound for example selected from the group of beta-secretase inhibitors; gamma-secretase inhibitors; gamma-secretase modulators; amyloid aggregation inhibitors such as e.g. alzhemed; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5 and/or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; metabotropic glutamate receptor 5 positive allosteric modulators; metabotropic glutamate receptor 2 antagonists, metabotropic glutamate receptor 2/3 agonists, metabotropic glutamate receptor 2 positive allosteric modulators and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance. At least one active substance is selected from the compounds according to the invention and/or the corresponding salts thereof. Preferably the composition comprises only one such active compound. In case of more than one active compound the other one can be selected from the aforementioned group of combination partners such as alzhemed, vitamin E, ginkolide, donepezil, rivastigmine, tacrine, galantamine, memantine, ibutamoren mesylate, capromorelin, minocyclin and/or rifampicin. Optionally the composition comprises further ingredients such as inert carriers and/or diluents.

The compounds according to the invention may also be used in combination with immunotherapies such as e.g. active immunisation with Abeta or parts thereof or passive immunisation with humanised anti-Abeta antibodies or antibody fragments for the treatment of the above mentioned diseases and conditions.

The compounds according to the invention also may be combined with Dimebon.

The compounds according to the invention also may be combined with antidepressants like amitriptyline imipramine hydrochloride (TOFRANIL), imipramine maleate (SURMONTIL), lofepramine, desipramine (NORPRAMIN), doxepin (SINEQUAN, ZONALON), trimipramine (SURMONTIL).

Or the compounds according to the invention also may be combined with serotonin (5-HT) reuptake inhibitors such as alaproclate, citalopram (CELEXA, CIPRAMIL) escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited. In the context of the present invention any suitable dosage form may be used. For example, the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently ⅕ of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.).

It is preferred that the compounds of the invention be administered either three or fewer times, more preferably once or twice daily.

EXAMPLES

Pharmaceutical Compositions

Examples which might illustrate possible pharmaceutical formulations, without being meant to be limiting:

The term "active substance" denotes one or more compounds according to the invention including the salts thereof. In the case of one of the aforementioned combinations with one or more other active substances the term "active substance" may also include the additional active substances.

Example A

Tablets Containing 100 Mg of Active Substance

Composition: tablet

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Example B

Tablets Containing 150 Mg of Active Substance

Composition: Tablet

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Example C

Hard Gelatine Capsules Containing 150 Mg of Active Substance

| | |
|---|---|
| active substance | 150.0 mg |
| lactose | 87.0 mg |
| corn starch (dried) | 80.0 mg |
| magnesium stearate | 3.0 mg |
| | 320.0 mg |

Example D

Composition: Suppository

| | |
|---|---|
| active substance | 150.0 mg |
| polyethyleneglycol 1500 | 550.0 mg |

-continued

| | |
|---|---|
| polyethyleneglycol 6000 | 460.0 mg |
| polyoxyethylene sorbitan monostearate | 840.0 mg |
| | 2000.0 mg |

Example E

Composition: Ampoules Containing 10 Mg Active Substance

| | |
|---|---|
| active substance | 10.0 mg |
| 0.01N hydrochloric acid | q.s. |
| double-distilled water | ad 2.0 mL |

Example F

Composition: ampoules containing 50 mg of active substance

| | |
|---|---|
| active substance | 50.0 mg |
| 0.01N hydrochloric acid | q.s. |
| double-distilled water | ad 10.0 mL |

The preparation of any the above mentioned formulations can be done following standard procedures.

Biological Assay

The in-vitro effect of the compounds of the invention can be shown with the following biological assays.

PDE9A2 Assay Protocol:

The PDE9A2 enzymatic activity assay was run as scintillation proximity assay (SPA), in general according to the protocol of the manufacturer (GE Healthcare, former Amersham Biosciences, product number: TRKQ 7100).

As enzyme source, lysate (PBS with 1% Triton X-100 supplemented with protease inhibitors, cell debris removed by centrifugation at 13.000 rpm for 30 mM) of SF 9 cell expressing the human PDE9A2 was used. The total protein amount included in the assay varied upon infection and production efficacy of the SF9 cells and lay in the range of 0.1-100 ng.

In general, the assay conditions were as follows:
total assay volume: 40 microliter
protein amount: 0.1-50 ng
substrate concentration (cGMP): 20 nanomolar; ~1 mCi/1
incubation time: 60 mM at room temperature
final DMSO concentration: 0.2-1%

The assays were run in 384-well format. The test reagents as well as the enzyme and the substrate were diluted in assay buffer. The assay buffer contained 50 mM Tris, 8.3 mM $MgCl_2$, 1.7 mM EGTA, 0.1% BSA, 0.05% Tween 20; the pH of assay buffer was adjusted to 7.5. The reaction was stopped by applying a PDE9 specific inhibitor (e.g. compounds according to WO 2004/099210 or WO 2004/099211, like one of the enantiomers of example 37, e.g. 1-(2-Chlorophenyl)-6-[(2R)-3,3,3-trifluoro-2-methyl-propyl]-1,5-dihydro-4H-pyrazolo[3,4-d]pyrimidine-4-one) in excess.

REFERENCES

Wunder F, Tersteegen A, Rebmann A, Erb C, Fahrig T, Hendrix M. Characterization of the first potent and selective PDE9 inhibitor using a cGMP reporter cell line. *Molecular Pharmacology*. 2005 December; 68(6):1775-81.

van der Staay F J, Rutten K, Bärfacker L, Devry J, Erb C, Heckroth H, Karthaus D, Tersteegen A, van Kampen M, Blokland A, Prickaerts J, Reymann K G, Schröder U H, Hendrix M. The novel selective PDE9 inhibitor BAY 73-6691 improves learning and memory in rodents. *Neuropharmacology*. 2008 October; 55(5):908-18.

PDE1C Assay Protocol:

The assay was run in an analogous manner to the PDE9A2 assay, with the following differences: instead of PDE9A2 PDE1C has been used and the assay buffer contained in addition 50 nM Calmodulin, 3 mM $CaCl_2$. The reaction can be stopped by applying the same inhibitor as the one that is outlined above (1-(2-Chlorophenyl)-6-[(2R)-3,3,3-trifluoro-2-methyl-propyl]-1,5-dihydro-4H-pyrazolo[3,4-d]pyrimidine-4-one).

Determination of $IC_{50}$:

$IC_{50}$ can be calculated with GraphPadPrism or other suitable software setting the positive control as 100 and the negative control as 0. For calculation of $IC_{50}$, dilutions of the test compounds (substrates) are selected and tested following the aforementioned protocol.

Data

In the following $IC_{50}$ values for PDE9A2 inhibition [nanomolar (nM)] illustrate that the compounds according to the present invention inhibit PDE9, specifically PDE9A2. This shows that the compounds provide useful pharmacological properties. The examples are not meant to be limiting.

The table also provides selectivity values (Selectivity) that show a preference of the compounds for PDE9A versus PDE1C. Selectivity is the ratio ($IC_{50}$ for PDE1C inhibition [nanomolar (nM)])/($IC_{50}$ for PDE9A2 inhibition [nanomolar (nM)]).

The example numbers refer to the final examples as outlined in the section Exemplary embodiments.

All data can be measured according to the procedure described herein. The definition enantiomer 1 or enantiomer 2 is refers to the elution orders of enantiomers in chiral SFC and chiral HPLC.

| Compound family | Example No. | $IC_{50}$ PDE9A2 [nanomolar] | Selectivity |
|---|---|---|---|
| A | 1* | 1 | 288 |
| A | 2 (trans enantiomer 1) | 0.5 | 532 |
| A | 3 (trans enantiomer 2) | 19 | 85 |
| C | 4* | 6 | 123 |
| D | 5* | 10 | 40 |

*trans racemic mixture

In-Vivo Effect:

It is believed that the positive in-vitro efficacy results of the compounds of the present invention translate in positive in-vivo efficacy.

The in-vivo effects of the compounds of this invention can be tested in the Novel Object Recognition test according to the procedure of Prickaerts et al. (*Neuroscience* 2002, 113, 351-361), the social recognition test or the T-maze spontaneous alternation test according to the procedures described by van der Staay et al. (*Neuropharmacology* 2008, 55, 908-918). For further information concerning biological testing one is also referred to these two citations.

Besides the inhibition property toward the target PDE9, compounds according to the present invention may provide further advantageous pharmacokinetic properties.

For example, compounds according to the invention may show one or more advantages in the area of safety, balanced metabolism, low risk of causing drug—drug interaction and/or balanced clearance.

Compounds also might show one or more additional or alternative advantages in the area of bioavailability, high fraction absorbed, blood brain transport properties, a favourable (e.g. high mean) residence time (mrt), favourable exposure in the effect compartment and so on.

CHEMICAL MANUFACTURE

Abbreviations

APCI Atmospheric pressure chemical ionization
ACN acetonitrile
DCM dichloromethane
DEA diethylamine
DIPEA diisopropylethylamine
DME 1,2-dimethoxyethane
DMF dimethylformamide
EI electronic impact
ESI electrospray ionization (in MS)
EtOH ethanol
Exp. Example
GC-MS gas chromatography with mass spectrometric detection
h hour(s)
HPLC high performance liquid chromatography
HPLC-MS coupled high performance liquid chromatography-mass spectrometry
M molar (mol/L)
MeOH methanol
min minutes
MS mass spectrometry
NMP 1-methyl-2-pyrrolidinone
$R_t$ retention time (in HPLC)
TFA trifluoroacetic acid
THF tetrahydrofuran
TLC thin-layer chromatography
HPLC ultra performance liquid chromatography
HPLC-MS Methods:
Method 1 ($NH_4COOH$)

Instrument: LC/MS Waters Acquity HPLC System DAD, SQD single quadrupole. Column: BEH C18 1.7 μm, 2.1 mm×50 mm; eluent A: water+ammonium formate 5 mM+10% acetonitrile; eluent B: acetonitrile; gradient: A 100%, then to B 100% in 1.20 min for 0.25 min; flow rate: 0.7 mL/min; UV detection: 254 nm; ion source: ESI.
LC-MS Methods:
Method 1
MS apparatus type: Waters Micromass ZQ; HPLC apparatus type: Waters Alliance 2695, Waters 2996 diode array detector; column: Varian Microsorb 100 C18, 30×4.6 mm, 3.0 μm; eluent A: water+0.13% TFA, eluent B: ACN; gradient: 0.0 min 5% B→0.18 min 5% B→2.0 min 98% B→2.2 min 98% B→2.3 min 5% B→2.5 min 5% B; flow rate: 3.5 mL/min; UV detection: 210-380 nm
Method 1E Hydro Instrument: LC/MS ThermoFinnigan. Hplc Surveyor DAD, MSQ Quadrupole; column: Synergi Hydro-RP80A, 4 um, 4.60×100 mm; eluent A: 90% water+10% acetonitrile+ammonium formate 10 mM; eluent B=ACN 90%+10% $H_2O$+$NH_4COOH$ 10 mM; gradient: A(100) for 1.5 min, then to B (100) in 10 min for 1.5 min; flow rate: 1.2 mL/min; UV Detection: 254 nm; Ion source: APCI.
Method 3

MS apparatus type: Waters Micromass ZQ; HPLC apparatus type: Waters Alliance 2695, Waters 2996 diode array detector; column: Varian Microsorb C18, 20×4.6 mm, 5.0 μm; eluent A: water+0.15 TFA, eluent B: MeOH; gradient: 0.0 min 5% B→0.25 min 5% B→1.90 min 100% B→2.05 min 100% B→2.15 min 5% B→2.25 min 5% B; flow rate: 5.2 mL/min; UV detection: 210-400 nm.
GC/MS Methods
Method 3A.2

Instrument: GC/MS Finnigan Thermo Scientific. Trace GC Ultra, DSQ II single quadrupole. Column: DB-5MS, 25 m×0.25 mm×0.25 μm; carrier gas: helium, 1 mL/min constant flow; oven program: 50° C. (hold 1 minute), to 100° C. in 10° C./min, to 200° C. in 20° C./min, to 300° C. in 30° C./min eluent, detection: trace DSQ II, single quadrupole; ion source: EI. Scan range: 50-450 a
Chiral HPLC Methods:
Chiral Method 1:

HPLC apparatus type: Agilent 1100; column: Daicel chiralcel OJ-H, 250 mm×4.6 mm, 5.0 μm; eluent: hexane/EtOH 80:20; flow rate: 1 mL/min, Temperature: 25° C.; UV Detection: variable (200-500 nm).
Microwave Heating:

Discover® CEM instruments, equipped with 10 and 35 mL vessels.
General Comment Concerning the Presentation of the Structures Some compounds have stereogenic centre(s). The structures depicted in the experimental section, below, will not necessarily show all the possible stereochemical possibilities of the compounds but only one. However, in such cases a term like "trans-racemic mixture" or "cis-racemic mixture" is added next to the depicted structure in order to indicate the other stereochemical options.

An example is given below. The presented structural formula is

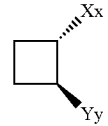

The added term "trans-racemic mixture" points to the second stereochemical option:

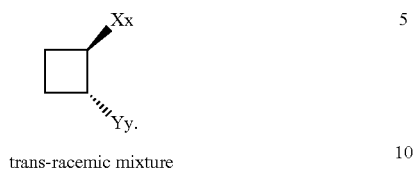

trans-racemic mixture

Thus, the manufactured compound is a mixture of

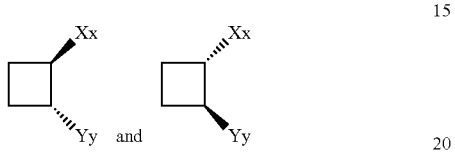

This principle applies to other depicted structures as well.

Example 1A

Cis-Racemic Mixture

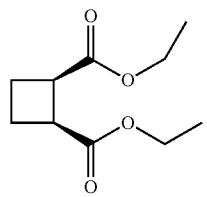

2.00 g (13.9 mmol) cis-cyclobutan-1,2-dicarboxylic acid were mixed with 15.5 mL EtOH at 0° C. and 2.15 mL (29.5 mmol) thionylchloride were slowly added. The mixture was allowed to warm to room temperature and stirred for 2 h. The solvent was removed under reduced pressure and the product was filtered through a pad of activated basic alumina that was afterwards washed with DCM. 2.70 g of the product were obtained.

GC (Method 3A.2): $R_t$: 8.42 min
MS (EI): m/z: 155 (M-45)$^+$, 127 (M-73)$^+$

The following example was synthesized in analogy to the preparation of Example 1A, using the corresponding diacid as starting material.

Example 2A

Trans-Racemic Mixture

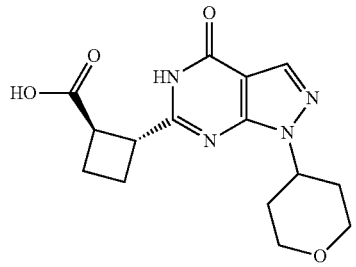 [SMILES: O=C(O)[C@@H]1CC[C@H]1c1nc2c(cnn2C2CCOCC2)c(=O)[nH]1]

1.17 g (5.5 mmol) 5-Amino-1-(tetrahydro-pyran-4-yl)-1H-pyrazole-4-carboxylic acid amide amide (see PCT patent application WO 09-121919) was mixed with 15 mL of anhydrous EtOH, 2.7 g (13.8 mmol) of Example 1A and 0.89 g (22.2 mmol) of sodium hydride (60% suspension in mineral oil) were added. The reaction mixture was heated to 140° C. for 40 min in a microwave oven (Power: 150 W). The mixture was cooled to room temperature, the solvent was removed under reduced pressure and the residue taken up with Citric Acid (5 ml of 10% solution in water); DCM was added and the organic phase was separated through a phase separator cartridge. The crude obtained after evaporation of solvents (2.18 g) was purified by flash-chromatography [Eluent: (DCM/MeOH/AcOH 90:10:1)/DCM] starting with DCM and eluting the final product with a 1/1 ratio of the above described eluent. 1.14 g (64%) of the product were obtained.

UPLC-MS (Method 1): $R_t$=0.54

MS (ESI pos): m/z=319 (M+H)$^+$

| Example | Structure | starting material | $R_t$ [min] | MS (ESI pos, m/z) |
|---|---|---|---|---|
| Exp. 1B trans-racemic mixture | 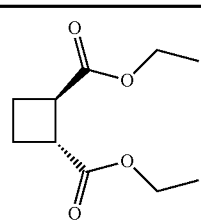 | | 1.34 (Method 1) | 201 (M + H)$^+$ |

Example 3A

Trans-Racemic Mixture

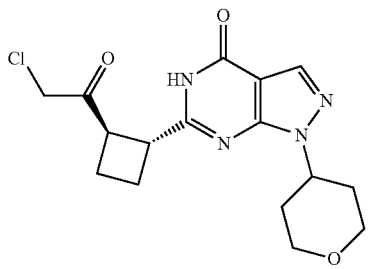 [SMILES: O=C(CCl)[C@@H]1CC[C@H]1c1nc2c(cnn2C2CCOCC2)c(=O)[nH]1]

0.50 g (1.76 mmol) of Example 2A were dissolved in THF (5 ml) under inert atmosphere; the temperature was lowered at 0° C. before the addition of DMF (1 drop) and oxalyl chloride (0.167 ml, 1.94 mmol). The reaction mixture was stirred 2 h at 0° C. and afterwards trimethylsilyldiazomethane (2M solution in diethyl ether) was added (1.76 ml; 3.52 mmol). After 2 h hydrochloric acid (4M solution in dioxane) was added (0.88 ml; 3.52 mmol) and the temperature increased to room temperature. The mixture was diluted with DCM and washed with NaHCO$_3$ saturated solution; the aqueous phase was extracted with DCM. The organic phases were collected and washed with NaCl saturated solution; the organic phase was dried and the residue obtained after evaporation of solvents (0.54 g) was used as such in the next steps.

UPLC-MS (Method 1): R$_t$=0.82
MS (ESI pos): m/z=351, 353 (M+H)$^+$

Example 4A

Trans-Racemic Mixture

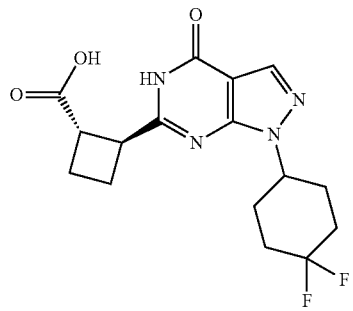

trans-racemic mixture 1.00 g (4.09 mmol) 5-Amino-1-(4,4-difluoro-cyclohexyl)-1H-pyrazole-4-carboxylic acid amide (see PCT patent application WO 2010/026214, example 8A) was mixed with 15 mL of anhydrous EtOH, 2.46 g (12.3 mmol) of Example 1B and 0.66 g (16.4 mmol) of sodium hydride (60% suspension in mineral oil) were added. The reaction mixture was heated to 140° C. for 30 min in a microwave oven. The mixture was cooled to room temperature and sodium hydroxide solution (4 M aqueous solution) was added. The solvent was removed under reduced pressure. The residue was purified by preparative HPLC (eluent A: water+0.13% TFA, eluent B: MeOH). 0.70 g (49%) of the product were obtained.

HPLC-MS (Method 1): R$_t$=1.24 min
MS (ESI pos): m/z=353 (M+H)$^+$

Example 5A

Trans-Racemic Mixture

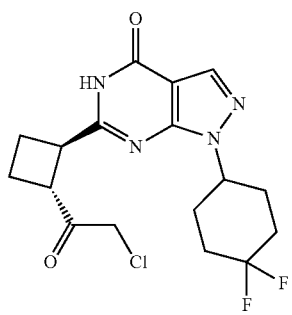

trans-racemic mixture 0.250 g (0.71 mmol) of Example 4A were mixed with 2 mL THF. The mixture was cooled with an ice bath and 0.060 mL (0.71 mmol) oxalylchloride and one drop of DMF were added. The reaction mixture was stirred at 0° C. for 1 h. To the reaction mixture were added 4 mL ACN and 0.710 mL trimethylsilyldiazomethane (2.0 M in hexane, 1.42 mmol). The mixture was stirred at 0° C. for 2 h, then 0.355 mL HCl (4.0 M in dioxane) was slowly added. The reaction was stirred for 15 min. To the mixture were added ethylacetate and saturated sodium hydrogen carbonate solution. The organic layer was washed with water and brine and partially evaporated. The product was used for the next reaction without further purification.

HPLC-MS (Method 1): R$_t$=1.40 min
MS (ESI pos): m/z=385/387 (Cl).

Exemplary Embodiments

Example 1

Trans-Racemic Mixture

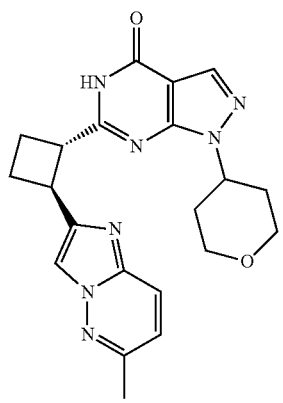 [SMILES: Cc1ccc2nc([C@H]3CC[C@@H]3c3nc4c(cnn4C4CCOCC4)c(=O)[nH]3)cn2n1]

Example 3A (1 g, 2.85 mmol) was suspended in dimethoxyethane in a 50 ml Schlenk tube; 3-amino-6-methylpyridazine was added; the Schlenk tube was closed with a stopper and the reaction mixture heated at 95° C. during 14 h.

The temperature was lowered, the solvent was removed under reduced pressure and the crude passed through a SPE "STRATA" 10 g SCX cartridge eluting with MeOH and afterwards with a $NH_3$ solution in MeOH; the obtained residue was purified by flash chromatography [EluentS: Cyclohexane/EtOAc (from 1/1 to 100% EtOAc), then EtOAc/MeOH (9/1)], yielding 0.69 g (59%) of the title compound.

HPLC-MS (Method 1Eh): $R_t$=7.62

MS (APCI): m/z=406 (M+H)$^+$

The enantiomers of Example 1 were separated by semipreparative chiral HPLC.

Method for semipreparative enantioseparation:

Semipreprative conditions:

HPLC semipreparative system: Waters 600 pump; column: Daicel chiralcel OJ-H, 5.0 μm, 250 mm×20 mm; eluent: hexane/EtOH 80:20; flow rate: 15 mL/min, Temperature: 25° C.; UV Detection: 230 nm

| Example | Structure | $R_t$ [min] |
|---|---|---|
| Exp. 2 trans-enantiomer 1 | 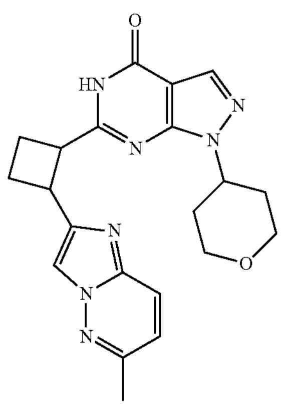 [SMILES: Cc1ccc2nc(C3CCC3c3nc4c(cnn4C4CCOCC4)c(=O)[nH]3)cn2n1] | 14.84 (Chiral Method 1) |
| Exp. 3 trans-enantiomer 2 | | 17.51 (Chiral Method 1) |

Example 4
Trans-Racemic Mixture

To Example 5A (crude product synthesized from 0.250 g (0.71 mmol) of Example 4A) was added dropwise 0.118 g (1.24 mmol) pyridin-2-ylamine in 4 mL EtOH. The reaction mixture was stirred overnight. The EtOH was evaporated and the residue was mixed with 2 ml DMF and heated to 50° C. for 2 h. The residue was purified by preparative HPLC (eluent A: water+0.13% TFA, eluent B: MeOH). After freeze drying the residue was diluted with 2 ml 10% aqueous $K_2CO_3$ and extracted with DCM. Evaporation of the solvent and freeze drying from ACN/water yielded 44 mg of the product.

HPLC-MS: (Method 3): $R_t$=1.20 min; MS (ESI pos): m/z=425 (M+H)$^+$

The following example was synthesized in analogy to the preparation of Example 4, using the corresponding amine as starting material.

| Example | structure | starting material: amine | Rt [min] | MS (ESI pos, m/z) |
|---|---|---|---|---|
| Exp. 5 trans-racemic mixture | 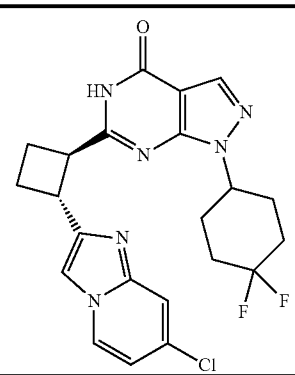 | 4-chlor-pyridin-2-ylamine | 1.21 (Method 3) | 459/61 (Cl) (M + H)$^+$ |

The invention claimed is:
1. A compound of formula (I)

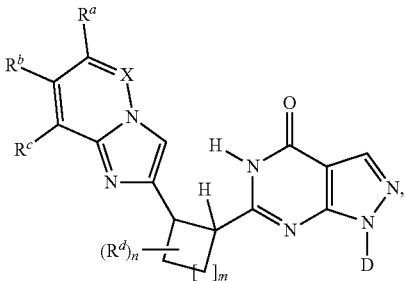

wherein
X is N or CR$^e$,
R$^a$, R$^b$, R$^c$ and R$^e$ are selected independently of each other from the group consisting of H, C$_{1-6}$-alkyl-, C$_{1-6}$-alkyl-O—, —CF$_3$, —CHF$_2$, —CH$_2$F, NC— and halogen;
   whereby C$_{1-6}$-alkyl- and C$_{1-6}$-alkyl-O— optionally may be substituted with halogen,
R$^d$: is selected from the group consisting of fluorine, NC—, —CF$_3$, —CHF$_2$, —CH$_2$F and methyl;
D: is selected from the group consisting of cyclopentyl, cyclohexyl, tetrahydrofuranyl, tetrahydropyranyl, 2-, 3- and 4-pyridyl,
   whereby cyclopentyl and cyclohexyl optionally may be substituted by 1 or 2 substituents, whereby said substituents may be selected independently of one another from the group consisting of fluorine, NC—, F$_3$C—, HF$_2$C— and FH$_2$C—;
   whereby tetrahydrofuranyl and tetrahydropyranyl optionally may be substituted by 1 or 2 substituents, whereby said substituents may be selected independently of one another from the group consisting of fluorine, NC—, F$_3$C—, HF$_2$C— and FH$_2$C—;
   whereby pyridyl optionally may be substituted by 1, 2, 3 or 4 substituents, whereby said substituents may be selected independently of one another from the group consisting of fluorine, chlorine, bromine, NC—, F$_3$C—, HF$_2$C—, FH$_2$C—, F$_3$C—CH$_2$—, C$_{1-6}$-alkyl- and C$_{3-7}$-cycloalkyl;
m: is selected from 1 or 2;
n: is selected from 0, 1 or 2,
   whereby if n=2, the two groups R$^d$ are selected independently of one another;
and salts thereof, solvates thereof and the solvates of the aforementioned salts thereof.

2. A compound according to claim 1,
wherein
X is N or CR$^e$,
R$^a$, R$^b$, R$^c$ and R$^e$ are selected independently of each other from the group consisting of H, C$_{1-3}$-alkyl-, C$_{1-3}$-alkyl-O—, —CF$_3$, —CHF$_2$, —CH$_2$F, NC— and halogen;
   whereby C$_{1-3}$alkyl- and C$_{1-3}$alkyl-O— optionally may be substituted with halogen,
R$^d$: is selected from the group consisting of fluorine, NC—, —CF$_3$, —CHF$_2$, —CH$_2$F and methyl;
D: is selected from the group consisting of cyclopentyl, cyclohexyl, tetrahydrofuranyl, tetrahydropyranyl, 2-, 3- and 4-pyridyl,
   whereby cyclopentyl and cyclohexyl optionally may be substituted by 1 or 2 substituents, whereby said substituents may be selected independently of one another from the group consisting of fluorine, F$_3$C—, HF$_2$C— and FH$_2$C—;
   whereby tetrahydrofuranyl and tetrahydropyranyl optionally may be substituted by 1 or 2 substituents, whereby said substituents may be selected independently of one another from the group consisting of fluorine, F$_3$C—, HF$_2$C— and FH$_2$C—;
   whereby pyridyl optionally may be substituted by 1, 2, 3 or 4 substituents, whereby said substituents may be selected independently of one another from the group consisting of fluorine, chlorine, bromine, NC—, F$_3$C—, HF$_2$C—, FH$_2$C—, F$_3$C—CH$_2$—, C$_{1-6}$-alkyl- and C$_{3-7}$-cycloalkyl;
m: is selected from 1 or 2;
n: is selected from the group consisting 0, 1 or 2,
   whereby if n=2, the two groups R$^d$ are selected independently of one another;
and salts thereof, solvates thereof and the solvates of the aforementioned salts thereof.

3. A compound according to claim 2,
wherein
X is N or CR$^e$,
R$^a$, R$^b$, R$^c$ and R$^e$ are selected independently of each other from the group consisting of H, methyl, ethyl, methoxy, ethoxy, CF$_3$—, —CHF$_2$, —CH$_2$F, NC— and halogen;
D: is selected from the group consisting of cyclopentyl, cyclohexyl, tetrahydrofuranyl, tetrahydropyranyl, 2-, 3- and 4-pyridyl,
   whereby cyclopentyl and cyclohexyl optionally may be substituted by 1 or 2 substituents, whereby said substituents may be selected independently of one another from the group consisting of fluorine, F$_3$C—, HF$_2$C— and FH$_2$C—;
   whereby tetrahydrofuranyl and tetrahydropyranyl optionally may be substituted by 1 or 2 substituents, whereby said substituents may be selected independently of one another from the group consisting of fluorine, F$_3$C—, HF$_2$C— and FH$_2$C—;
   whereby pyridyl optionally may be substituted by 1, 2, 3 or 4 substituents, whereby said substituents may be selected independently of one another from the group consisting of fluorine, chlorine, bromine, NC—, F$_3$C—, HF$_2$C—, FH$_2$C—, F$_3$C—CH$_2$—, C$_{1-6}$-alkyl- and C$_{3-7}$-cycloalkyl;
m: is selected from 1 or 2;
n is 0,
and salts thereof, solvates thereof and the solvates of the aforementioned salts thereof.

4. A compound according to claim 1,
wherein
X is N or CR$^e$,
R$^b$, R$^c$ and R$^e$ are each H,
R$^a$ is selected from the group consisting of H, methyl, ethyl, methoxy, ethoxy, —CF$_3$, —CHF$_2$, —CH$_2$F and F;
D: is selected from the group consisting of cyclopentyl, cyclohexyl, tetrahydrofuranyl, tetrahydropyranyl, 2-, 3- and 4-pyridyl,
   whereby cyclopentyl and cyclohexyl optionally may be substituted by 1 or 2 substituents, whereby said substituents may be selected independently of one another from the group consisting of fluorine, F$_3$C—, HF$_2$C— and FH$_2$C—;
   whereby tetrahydrofuranyl and tetrahydropyranyl optionally may be substituted by 1 or 2 substituents, whereby said substituents may be selected independently of one another from the group consisting of fluorine, F$_3$C—, HF$_2$C— and FH$_2$C—;
   whereby pyridyl optionally may be substituted by 1, 2, 3 or 4 substituents, whereby said substituents may be selected independently of one another from the group consisting of fluorine, chlorine, bromine, NC—, F₃C—, HF₂C—, FH₂C—F₃C—CH₂—, C₁₋₆-alkyl- and C₃₋₇-cycloalkyl;

m: is selected from 1 or 2;

n is 0, and salts thereof, solvates thereof and the solvates of the aforementioned salts thereof.

5. A compound according to claim 1, wherein m=1.

6. A compound according to claim 1, wherein X═N.

7. A compound according to claim 1, wherein X═CRᵉ.

8. A compound according to claim 1, wherein D is either 4,4-difluorocyclohexyl, tetrahydropyran-4-yl or 4-methyl-3-pyridyl, wherein none of these two groups has further substituents and m=1.

9. A compound according to claim 1, wherein the compound is selected from the group consisting of

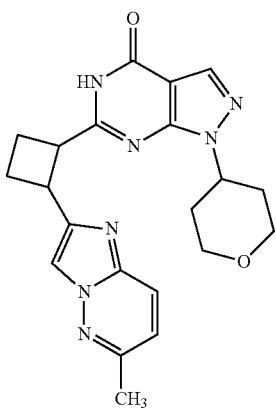

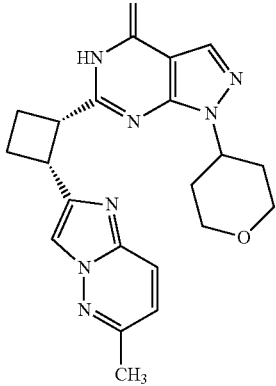

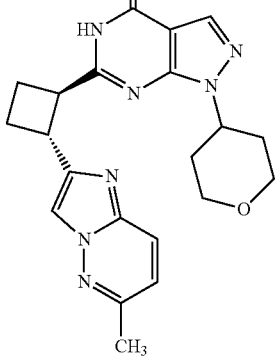

-continued

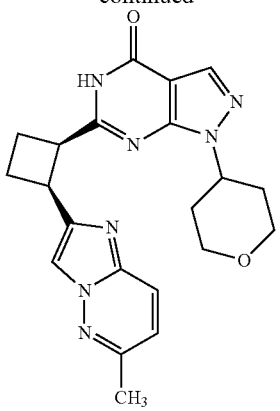

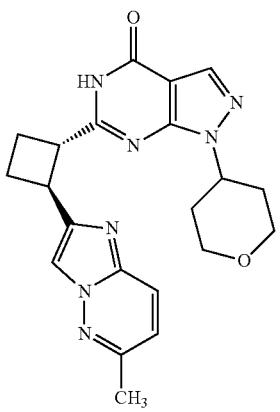

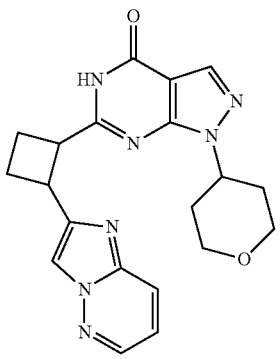

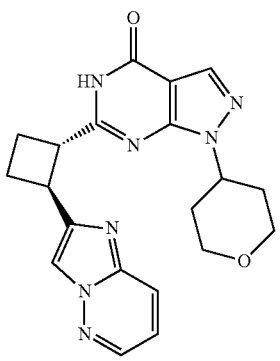

41
-continued
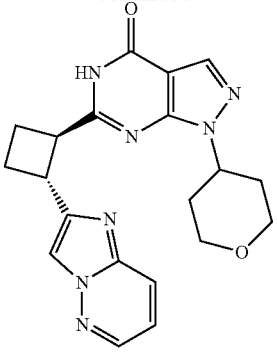
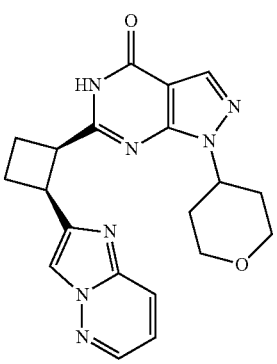
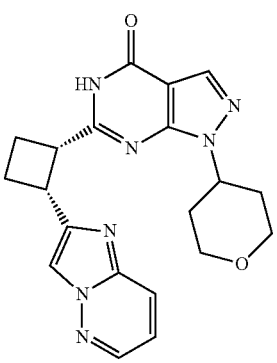
and pharmaceutically acceptable salts thereof.
10. A compound according to claim 1, wherein the compound is selected from the group consisting of
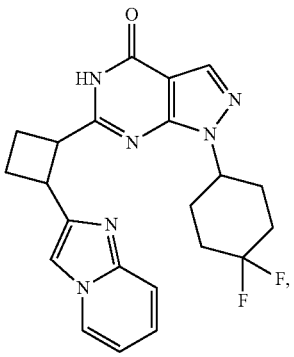
42
-continued
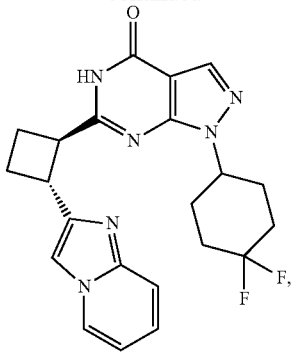
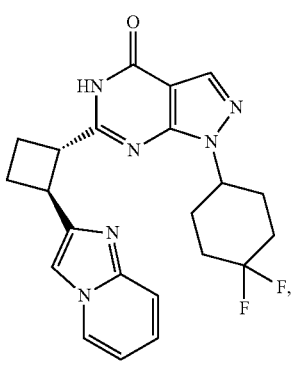
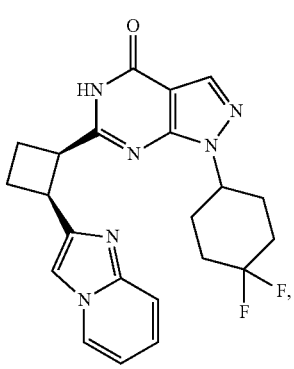
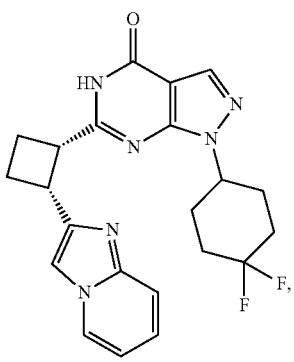

-continued
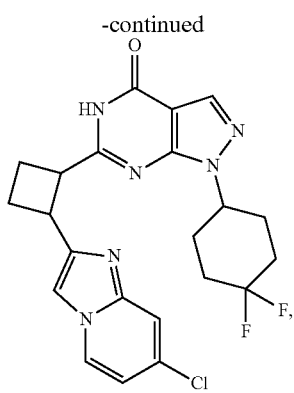
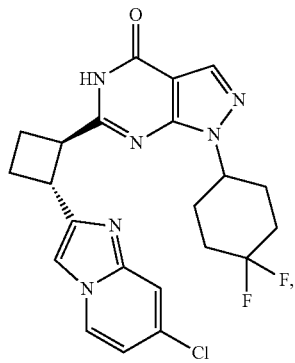
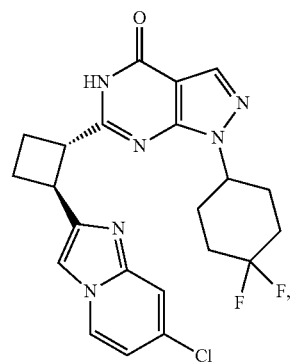
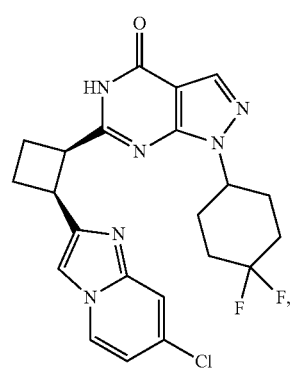
-continued
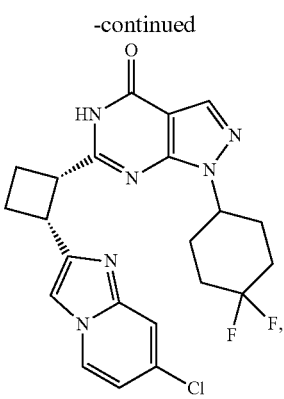
and pharmaceutically acceptable salts thereof.
11. A compound according to claim 1, wherein the compound is selected from the group consisting of a compound according to formula (Ia), formula (Ib), formula (Ic) and formula (Id)
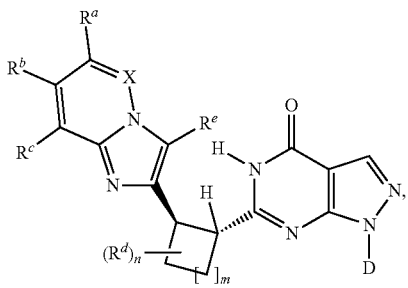
(Ia)
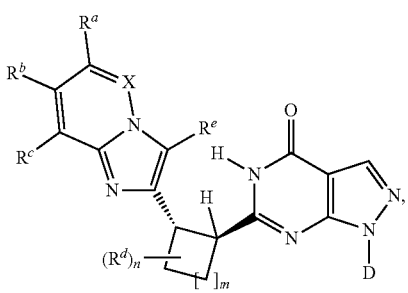
(Ib)
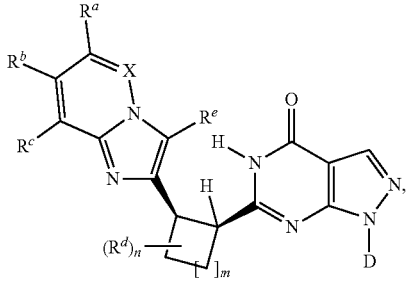
(Ic)

-continued
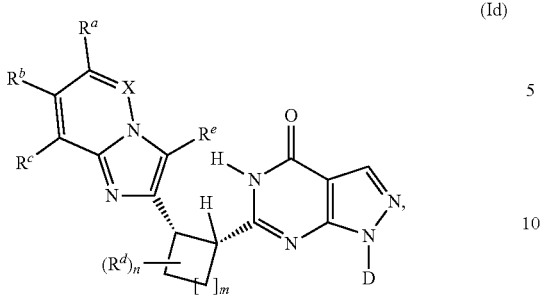
(Id)
wherein $R^a$, $R^b$, $R^c$, $R^d$, $R^e$, D, m and n are as defined in claim 1,
and pharmaceutically acceptable salts thereof.
12. A pharmaceutical composition comprising a compound according to claim 1 and a pharmaceutical carrier.
13. A pharmaceutical composition comprising a compound according to claim 1 and another active substance.
* * * * *